United States Patent
Kandlikar et al.

(10) Patent No.: US 11,010,898 B2
(45) Date of Patent: May 18, 2021

(54) DETECTION AND CHARACTERIZATION OF CANCEROUS TUMORS

(71) Applicant: Bired Imaging, Inc., Rochester, NY (US)

(72) Inventors: Satish G. Kandlikar, Rochester, NY (US); Donnette Dabydeen, Pittsford, NY (US); Lori Medeiros, Pittsford, NY (US); Pradyumna Phatak, Pittsford, NY (US); Jose Luis Gonzalez Hernandez, Rochester, NY (US); Alyssa Owens, East Rochester, NY (US)

(73) Assignee: Bired Imaging, Inc., Rochester, NY (US)

( * ) Notice: Subject to any disclaimer, the term of this patent is extended or adjusted under 35 U.S.C. 154(b) by 17 days.

(21) Appl. No.: 16/439,192

(22) Filed: Jun. 12, 2019

(65) Prior Publication Data
US 2019/0385308 A1     Dec. 19, 2019

Related U.S. Application Data

(60) Provisional application No. 62/684,284, filed on Jun. 13, 2018, provisional application No. 62/727,146, filed on Sep. 5, 2018.

(51) Int. Cl.
*G06K 9/00* (2006.01)
*G06T 7/00* (2017.01)
(Continued)

(52) U.S. Cl.
CPC ............ *G06T 7/0014* (2013.01); *A61B 5/015* (2013.01); *A61B 5/4312* (2013.01); *A61B 5/489* (2013.01);
(Continued)

(58) Field of Classification Search
CPC .......... G06T 7/0014; G06T 7/30; G06T 7/62; G06T 7/0012; G06T 7/0016; G06T 7/11;
(Continued)

(56) References Cited

U.S. PATENT DOCUMENTS 5,961,466 A   10/1999  Anbar
7,510,532 B2   3/2009  Mitra
(Continued)

FOREIGN PATENT DOCUMENTS

WO   2017184201    10/2017

OTHER PUBLICATIONS

Kwok, J et al. Thermal Imaging and Analysis for Breast Tumor Detection. BEE 453: Computer-Aided Engineering: Applications to Biomedical Processes. May 2007; <https://ecommons.cornell.edu/bitstream/handle/1813/7913/group11.pdf?sequences=1&isAllowed=y>.

(Continued)

*Primary Examiner* — Jose L Couso
(74) *Attorney, Agent, or Firm* — Joseph M. Noto; Bond, Schoeneck & King, PLLC

(57) ABSTRACT

Processes and techniques are disclosed to identify regions of suspected malignancy and their localization within a body part or organ. These methods rely on the analysis of infrared images to identify thermal abnormalities using image post-processing techniques, numerical modeling, iterative solutions methodology or a digital library. The methods utilize noninvasive, non-radiative and no contact infrared imaging that can be used for breast cancer screening for improved prognosis.

17 Claims, 29 Drawing Sheets

(51) Int. Cl.
*A61B 5/01* (2006.01)
*A61B 5/00* (2006.01)
*G06T 17/00* (2006.01)
*G06T 7/30* (2017.01)
*G06T 7/62* (2017.01)

(52) U.S. Cl.
CPC .................. *G06T 7/30* (2017.01); *G06T 7/62* (2017.01); *G06T 17/00* (2013.01); *G06T 2207/10048* (2013.01); *G06T 2207/10088* (2013.01); *G06T 2207/10116* (2013.01); *G06T 2207/10132* (2013.01); *G06T 2207/20221* (2013.01); *G06T 2207/30068* (2013.01); *G06T 2207/30096* (2013.01)

(58) Field of Classification Search
CPC . G06T 17/00; G06T 3/00; G06T 2207/30096; G06T 2207/10048; G06T 2207/10132; G06T 2207/10088; G06T 2207/10116; G06T 2207/20221; G06T 2207/30068; G06T 2207/30088; G06T 2207/20108; G06T 2207/30204; A61B 5/015; A61B 5/489; A61B 5/4312; A61B 5/1075; A61B 5/708; A61B 5/444; A61B 5/7275; A61B 5/0091; A61B 5/0073; A61B 5/0064; A61B 5/0075; A61B 5/0086; A61B 5/0008; A61B 5/0013; A61B 2576/02; A61B 10/0041; A61B 8/00; A61B 8/5223; G16H 30/40; G16H 50/20; G16H 50/30; G01J 2005/0077; G01J 2005/0081; G06K 9/3233; G06K 9/46; G06K 9/4604; G06K 9/6267; G06K 9/0014; G06K 9/00147; G06K 2209/05; Y10S 128/922; G06F 19/00; G06F 19/321
See application file for complete search history.

(56) References Cited

U.S. PATENT DOCUMENTS

| | | | |
|---|---|---|---|
| 8,185,357 | B1 | 5/2012 | Szu et al. |
| 8,475,377 | B2 | 7/2013 | Angott |
| 8,913,803 | B2 | 12/2014 | Arnon |
| 10,055,542 | B2 | 8/2018 | Venkataramani et al. |
| 10,368,846 | B2* | 8/2019 | Venkataramani ...... A61B 5/489 |
| 2007/0213617 | A1 | 9/2007 | Berman |
| 2008/0077019 | A1* | 3/2008 | Xiao ................... A61B 5/0064 600/474 |
| 2009/0048523 | A1 | 2/2009 | Schlagheck et al. |
| 2010/0191541 | A1 | 7/2010 | Prokoski |
| 2010/0312136 | A1* | 12/2010 | Cozzie ................... G16H 30/20 600/549 |
| 2011/0021944 | A1* | 1/2011 | Arnon ................... A61B 5/015 600/549 |
| 2011/0230942 | A1* | 9/2011 | Herman ............... A61B 5/0059 607/96 |
| 2011/0243409 | A1* | 10/2011 | Naimi .................. A61B 5/0091 382/128 |
| 2013/0116573 | A1* | 5/2013 | Herman ............... A61B 5/0064 600/474 |
| 2014/0112561 | A1 | 4/2014 | Arnon et al. |
| 2015/0182121 | A1 | 7/2015 | Barbour et al. |
| 2016/0278641 | A1 | 9/2016 | Venkataramani |
| 2017/0027450 | A1 | 2/2017 | Toledano et al. |

OTHER PUBLICATIONS

International Search Report and Written Opinion for International Application No. PCT/US2019/36758; dated Oct. 24, 2019.
Bezerra, et al. Estimation of breast tumor thermal properties from infrared images. Signal Processing/2013, pp. 1-13.
Jiang et al. Modeling static and dynamic thermography of the human breast under elastic deformation. Physics in Medicine and Biology/2011 pp. 1-17.
Francis et al. Breast cancer detection in thermography images using texture features. Infrared Physics and Technology/2014 pp. 1-7.

* cited by examiner

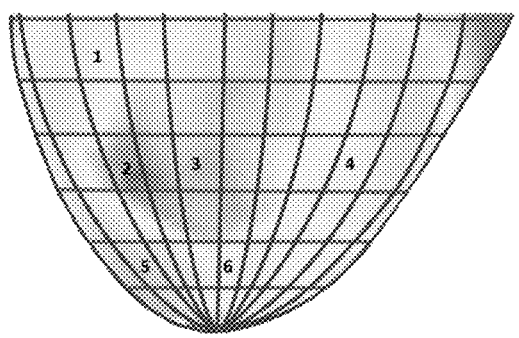
| Region | $T_{mean}$ [°C] | $T_{max}$ [°C] | $T_{min}$ [°C] | SD [°C] |
|---|---|---|---|---|
| 1 | 30.3 | 30.6 | 30.1 | 0.1033 |
| 2 | 32 | 33.3 | 30.6 | 0.5940 |
| 3 | 31.6 | 32 | 31 | 0.1827 |
| 4 | 30.5 | 30.8 | 30.1 | 0.1049 |
| 5 | 29.3 | 29.9 | 28.8 | 0.2040 |
| 6 | 30.2 | 30.6 | 29.8 | 0.1150 |
Fig. 12A                    Fig. 12B

| Patient | IR image | Simulated | Actual | Estimated |
|---|---|---|---|---|
| 3 | 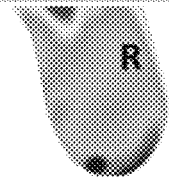 | 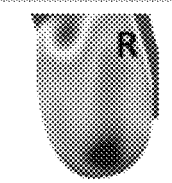 | d = 10<br>x = 52<br>y = 81<br>z = 118 | d = 10<br>x = 52<br>y = 78<br>z = 120 |
| 6 | 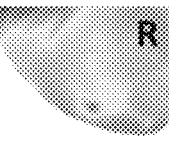 | 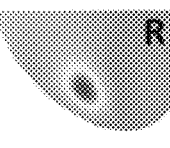 | d = 27<br>x = 95<br>y = 130<br>z = 110 | d = 27.2<br>x = 96<br>y = 129<br>z = 108 |
| 7 | 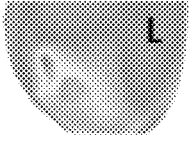 | 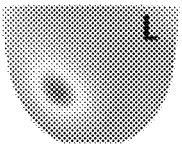 | d = 20<br>x = 121<br>y = 130<br>z = 167 | d = 19.1<br>x = 120<br>y = 132<br>z = 164 |
Fig. 26

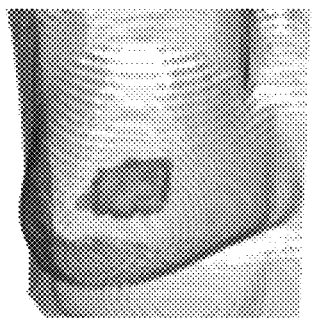 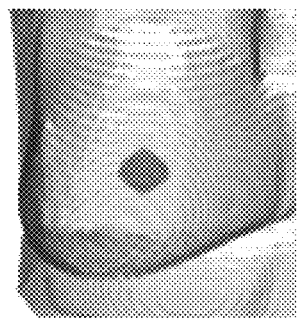 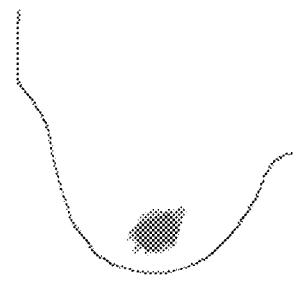
Actual Tumor Within Breast     Estimated Tumor Within Breast     Tumor Registration
Fig. 27

DETECTION AND CHARACTERIZATION OF CANCEROUS TUMORS

CROSS REFERENCE

This application claims the benefit of the filing date of U.S. Provisional Patent Application Ser. No. 62/684,284, filed Jun. 13, 2018, and this application claims the benefit of the filing date of U.S. Provisional Patent Application Ser. No. 62/727,146, filed Sep. 5, 2018, which are hereby incorporated by reference in its entirety.

This invention was made with government support under grant number CBET-1640309 awarded by National Science Foundation. The government has certain rights in this invention.

FIELD

The present disclosure relates to methods for detection and characterization of cancerous tumors.

BACKGROUND

Breast cancer (BC) is the most common form of cancer among women in the U.S., with more than 246,000 new cases diagnosed in 2018. It is estimated that one in every eight women (12.5%) will develop BC during her lifetime and that one in every 24 woman (4.16%) will die of BC. Early detection of BC is crucial to increase the survival of individuals; since 2003, the mortality rate has dropped ~1.2% annually mainly due to improvements in detection and treatment. Improving BC screening techniques for more accurate early detection will save lives. The exact reasons for developing BC have not been determined, but researchers agree that age and breast density are two of the most important factors that increase the risk. In the U.S., ~80% of individuals diagnosed with cancer are at least 50 years old. The risk of developing cancer is six times greater for women with more than 60% dense tissue as compared to women with ~30% dense tissue; approximately >40% women have dense breast tissue. There are a variety of screening techniques available to detect BC. However, mammography, the most accepted and widely used, is suboptimal in breasts with dense tissue (found in 40-50% of women). Digital breast tomosynthesis (DBT), similar to mammography, is being explored to improve cancer detection, however it suffers from subject discomfort, higher cost and increased radiation exposure. Magnetic Resonance Imaging (MRI) is an option but is time consuming and too expensive to be used for general screening and as such is limited to high risk populations (lifetime risk >20%) by most insurers. Ultrasound is one of the most commonly used adjuncts for the general population; however, it is very operator dependent and findings may be difficult to reproduce.

Infrared Imaging (IRI) has the potential to detect thermal signatures that allow for detection of BC with less likelihood of dense breast tissue masking the tumor. IRI captures the heat emitted by the breast surface and generates a thermal image, which is altered by the presence of a tumor. Dynamic IRI, with a cold air blast on the breast surface, induces discomfort and is ineffective for deeper tumors. Steady-state IRI is painless and does not expose subjects to radiation. Since IRI does not require special equipment other than the IR camera and positioning stand, it can be easily incorporated into existing mammography centers. However previous usage of this technique reported in literature is not founded on rigorous scientific approach.

Various methods to detect and analyze thermal contours include thermal trajectories, contouring and thermal indices. One study described a method to determine a 3D thermally distinguishable region. The method consists of obtaining a thermal image defined over a 3D spatial representation of a living body. Later, spots are identified in the thermal image and a thermal path is calculated. At least two thermal trajectories (paths) are used to determine at least one internal 3D thermally distinguishable region. Another invention created a method for detecting, diagnosing and guiding treatment of cell irregularities in an examined tissue. The steps of the method are: applying thermo-modulating means to at least a portion of said examined tissue (cooling or warming), collecting thermal data of the tissue, and calculating at least one heat transfer index over time (between 10 ns and 10 s). The thermal index is computed as the derivative of any order of such thermal index over time. The thermal index is normalized in a scale between 1 and 10, where higher values indicate more severity of the cell irregularities. The index is associated with malignant tumor, precancerous tumors, benign tumors, infections, pneumonia, necrotic cells and any combination thereof. The indexes are computed in a pixel or set of pixels with salient thermal characteristics. These techniques are often simplistic, not reliable due to lack of scientific rigor, or rely on operator experience to identify suspicious tumors.

Other methods explore a combination of techniques in order to adequately compare surface features. Some inventors developed a system using both IR imaging and x-rays. The device is housed inside a closed chamber, where both acquisition systems are used simultaneously. Patients are imaged in prone position without compression. The device is used to correlate anatomical and physiological characteristics and post process analysis in order to reduce the number of false positives. The device has multiple IR cameras, one of the cameras is aligned parallel to the x-ray source, other IR camera is aligned perpendicular to the x-ray source, other positions of the IR camera can be used to obtain cranial, medial, candid, lateral and frontal images. The x-ray and the IR cameras can rotate around the opening and can be moved along the x and y axes. Another invention made a system and methods to improve the performance of breast IR imaging by employing a combination of near IR and mid IR frequencies for detection of cancer and other subsurface defects. The system also contains an IR transparent window that can be used to distort the breasts or impose an artificial heat flow to and from the breasts. Near IR provides information about deeper structures because it is a penetrating wavelength and mid IR provide information about surface characteristics. The device uses a source of mid IR wavelength such as led lamps. Some inventors created a similar system that consists of thermal and electrical impedance scanning together. The novelty of their invention is the frequency dependence of the electrical impedance of the tissue, which allows the acquisition of multiple thermal images with currents at different frequencies injected in the region under inspection. The method without application of electrical current provides conventional thermal images. The application of electrical current enhances the thermal contrast in the surface, depending on the electrical properties of the tissue. The IR detector must operate in two bands (MWIR and LWIR). The images without electric current and with electric stimulation are compared at different frequencies. Electrodes are attached to the surface for delivering the electric current. Another used a device for multi-modality test of breast cancer utilizing thermography, ultrasound and optical spectroscopy.

SUMMARY

In accordance with one aspect of the present disclosure, there is provided a method of obtaining infrared images, generating thermal indicators from an infrared image of a body part and identifying suspected malignancy.

In accordance with another aspect of the present disclosure, there is provided a method to localize suspected malignancy within a body part by generating a 3D digital model and comparing phantom thermal images with surface infrared images.

In accordance with another aspect of the present disclosure, there is provided a method to generate a digital library with geometric and thermal identifiers of various body parts for comparison with clinical images.

These and other aspects of the present disclosure will become apparent upon a review of the following detailed description and the claims appended thereto.

BRIEF DESCRIPTION OF THE DRAWINGS

FIG. 12A is a thermal grid composed of latitudinal and longitudinal lines on a breast infrared image and FIG. 12B shows statistical indicators in selected regions of the grid;

FIG. 26 illustrates tumor location and size estimation for different cases;

FIG. 27 shows a series of volumetric images of breast with actual tumor, estimated tumor and registration;

DETAILED DESCRIPTION

Figure 1:
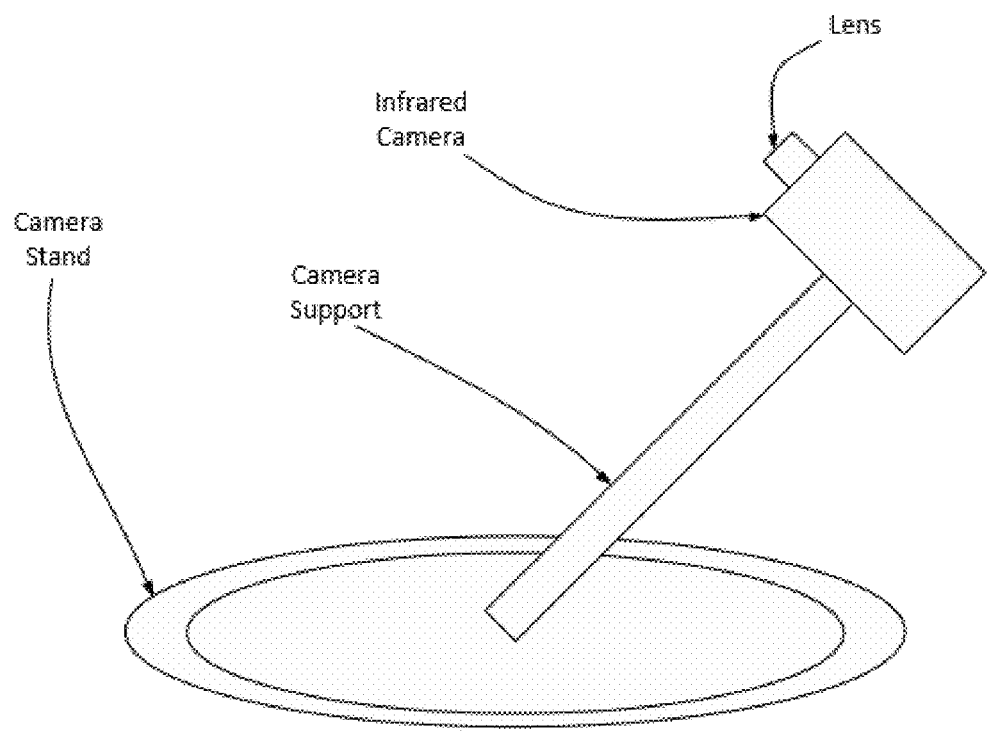
FIG. 1 illustrates a camera table setup with turntable in accordance with an embodiment.

Thermography is able to detect malignant tumors in tissues in a body part, such as the breast, based on temperature variation due to increased vasculature (angiogenesis) and increased blood perfusion to the affected area. The terms Thermography, infrared imaging, IR imaging and IRI are used interchangeably to mean images obtained in the infrared frequency range. The temperature profiles that result from IR imaging show any temperature variation over the body part surface, including those resulting from random vasculature especially near the body part surface, tumors, hormonal changes, and outside influencing factors such as alcohol/coffee consumption, clothing changes, makeup and deodorant/lotion. The present disclosure deals with providing geometric and thermal identifiers, specific markers and techniques to identify the presence and size/location of malignant tumors from the infrared images of the body part. These images are obtained by an infrared (IR) camera. Although the disclosure is described in greater detail using the female breasts and breast cancer, the disclosure covers the presence of suspected malignancy in any tissue in the body. Suspected malignancy refers to an area of suspicious cellular activity indicative of cancer. These may be obtained under steady-state or dynamic conditions using steady-state or dynamic Infrared Imaging (IRI). This disclosure describes various methods for malignancy detection in tissue. Breast cancer is an ideal candidate for IR imaging because the breasts lie in between the chest wall and the environment. There is no empty space in the body for other factors to block or alter the resulting thermal images. IR imaging could be incredibly beneficial for other diseases with a similar ideal setting. Examples of other potential diseased tissue that can benefit from this technology are listed. Thyroid Cancer—Thyroid cancer is rarer in the United States compared to breast cancer and colon cancer. It is also highly treatable with a low mortality rate. Similar to breast cancer, it is often initially discovered through self-examination. A lump or nodule discovered in the thyroid leads to an ultrasound and biopsy before cancer is diagnosed. Detecting the early signs of thyroid cancer can be challenging. Although the prognosis of thyroid cancer is very good, early detectability is always an issue. Because the thyroid is located close to the neck surface, surface thermal imaging would be simple. Skin Cancer—Although much of skin cancer can be visually assessed, rarer forms of skin cancer can be harder to diagnose. Skin cancer involves lesions, bumps, inflammation, or internal disease. Determining the extent of the cancer and later stage metastasis such as lymph node involvement is where imaging techniques are needed and where IR imaging could particularly come into play. Testicular Cancer—Testicular cancer is a rarer form of cancer with only approximately 20,000 cases in the United States per year. Similar to breast cancer, detection is similar by feeling a lump in either testicle. Due to the similar properties of the breast and breast cancer, IRI could easily be implemented to screen for testicular cancer. Non-Cancerous Diseases—The heat and increased blood perfusion associated with malignant tissue provides a good environment for thermal imaging. Other diseases, such as inflammatory diseases, are also strong contenders for this diagnosis modality. Diseases such as neuropathy, joint inflammation and arthritis, and various bowel diseases have been imaged using IR imaging.

Breast cancer-related mortality rates in the United States have decreased due to advancements in screening and treatment. The prevalence of breast cancer in the United States is higher than in the developing countries. However, the mortality to incidence ratio in developing countries is higher. Although some cancers are easily detected after progression and metastasis, the survival rates become much lower. An increase in annual breast screening could dramatically improve survival rates in developing countries. However, the current techniques for breast cancer screening are expensive, not portable, adversely affected by the presence of dense tissue and cannot be easily adapted in remote locations. Thermal imaging can easily be made portable for implementation in remote or rural setting. With today's updated technology, some of the infrared cameras are compact enough to connect to a smartphone. Potential future application could include the development of a mobile application for onsite analysis of infrared images during screening. The only additional needed equipment is a seat or stool and an added support system to screen someone in the prone position with the breasts hanging freely, without gravitational deformation often seen in supine or seated positions. Portable infrared imaging camera is used in specific orientations including but not limited to frontal, oblique views, downward looking, upward looking on the body part being imaged. A body part refers to any body part or organ in both humans and animals that can be clinically imaged. Resulting images can be transmitted to an image processing center for further evaluation. The images can be further processed using the technique described below, and suspicion is determined. The results can be discussed with the consulting physician and further evaluation can be prescribed for thermal abnormality identification and specification.

Although prone position is desirable to image the breast, other positions used in IR imaging can be used for detecting cancer using this invention. The wireless connectivity and ability to transmit the images to a central station where the images are used for further analysis using detection software, including the ones from this disclosure will further improve the early detection rate.

Throughout the IR imaging and detection process, there are many key steps. The patient enters the room and is screened. IRI involves the acclimation of the body part to be imaged in order for steady state to be reached. Acclimation includes quasi-steady state conditions where temperatures are reasonably steady over a sufficient time, including a ten to twenty minute duration, five to ten minute duration, or one to five minute duration. Once the imaging begins, it involves the capturing of from 1-20 images or more around the body part. The images are used to identify abnormalities associated with malignancy. The images can be further processed using software techniques and numerical simulation tools to characterize the tumor. Tumor characterization involves identifying at least one or at least several of the parameters such as tumor size, tumor location, tissue thermal properties, metabolic heat generation of the tumor, metabolic heat generation of the non-cancerous tissue, fat layer thickness, and fat layer thermal properties. Some further characterization involves shape of the tumor.

An example of this method uses the breast and IRI to detect malignancy. The IR imaging table can also be redesigned for other bodily purposes, for medical reasons, for comfort, etc. including but not limited to, adjustments in the center of the table for subjects who are morbidly obese or pregnant, subjects who cannot be in the specific position, subjects who would rather be kneeling, etc. The specific position includes upright, supine, lying sideways, or prone position dependent on the body part being imaged. In the instance of screening for breast cancer, when a subject enters the infrared imaging room, she is requested to disrobe from the waist up. Although the subject is generally female, the technique can be used for other genders. The technique can be used for other living species including but not limited to dogs, cats, horses, etc. A hospital gown for privacy is given and worn with an opening in the front. The subject lies down on the table in the prone position with one breast placed in the opening in the table. A period of, for example, 10 minutes is allowed for proper acclimation from the surrounding room temperature. This period may be increased or decreased depending on the acclimation time needed for the breast surface to reach near thermal equilibrium state with the surroundings. Prior to imaging, subjects are asked a variety of questions to determine if any external factors will affect the resulting images. They may be asked some or all of the questions, or other questions designed to get the relevant information related to each question. Additional relevant questions that affect the thermal profile may also be asked. For example, when screening for breast cancer, the following questions are discussed with the patient:

Have you sunbathed within five days prior to the exam?

Have you used lotion/cream, makeup, deodorant on the breasts on the day of the exam?

Have you exercised today?

Have you smoked or had alcohol today?

Have you had coffee or tea today?

Were you wearing tight-fitted clothing?

Are you post-menopausal? If not, what is the current day of your menstrual cycle? When was your last period? Do you have a regular cycle?

Are you on birth control? If so, what type?

Did you have a previous or a recent injury to your breast?

Did you recently have surgery?

Did you have any surgery on breast?

Do you have a fever?

When steady state is reached, infrared imaging begins. Images are taken, beginning at the head, separated by 45° looking up at 25° angle to vertical. The process of taking each image may only take about 30 seconds-1 minute. Shorter or longer duration may be needed depending on the camera and imaging setup. One example of a camera mount is shown in FIG. 1 but the camera setup can be created in a number of ways. The resolution of a suitable IR camera that is used is 640×512 pixels, with a thermal sensitivity of 0.02° C. (FLIR SC6700). Other cameras that provide the necessary thermal information may be used with different pixel sizes and resolution. The angle and focus of the camera varies based on the tissue being screened. Other angles to vertical orientation and angular separation may be used to obtain specific or detailed images of the body part.

Figure 2:
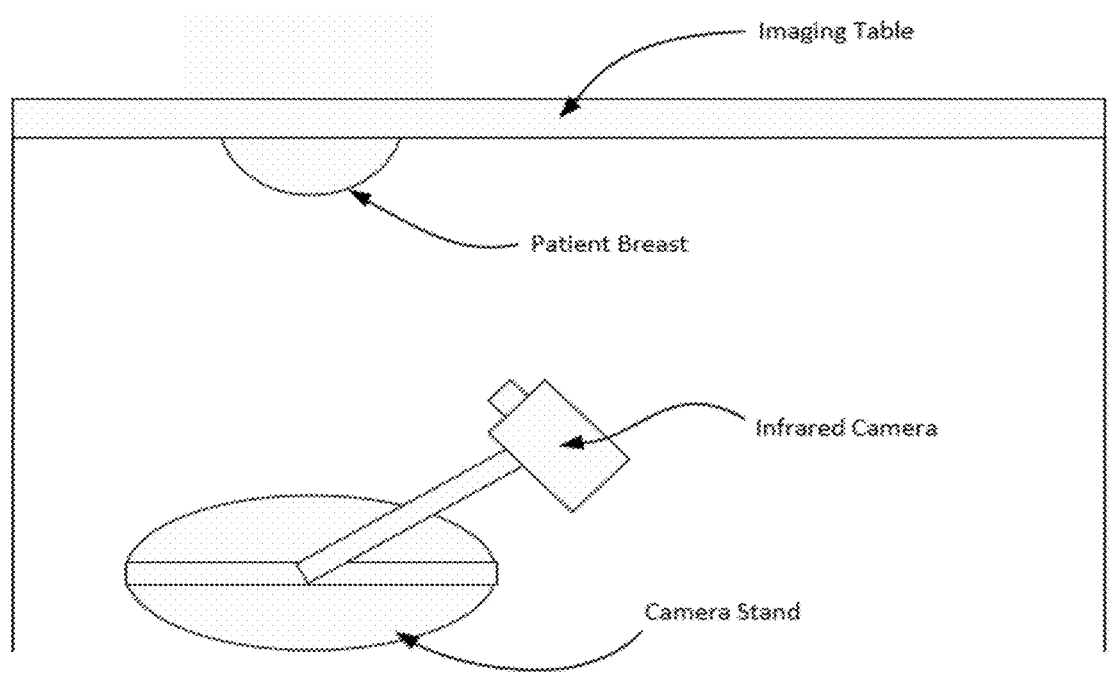
FIG. 2 illustrates an embodiment of an infrared imaging breast imaging table with camera setup underneath.

In order to obtain images of potentially suspicious tissue, an imaging table is used to facilitate screening. This table can be designed in a multitude of ways dependent on the tissue being imaged and can be modular to fit many body types or abnormalities. In the example of imaging breast cancer, using imaging positions such as the supine and upright positions, imaging the breasts with infrared imaging can cause unwanted thermal distortions in the inframammary fold, between the breast and the underside of the breasts. Examples of some table designs used to screen the female breast for breast cancer are discussed further. One such embodiment, seen in FIG. 2, involves a table with a circular opening where the breasts are exposed to an IR camera mounted on a stand that moves on a circular track. The purpose of the table is to facilitate obtaining infrared images in the desired view of the breast. The imaging table is a retrofitted lab table with a 9-inch hole for the breast imaging. A 2-inch layer of foam is placed on top for comfort and a layer of disposable paper is used for cleanliness. A black curtain was added around the edge of the table to hide the camera equipment and ensure no reflection or stray thermal artifacts during imaging. Additional acclimation time may be given for the acclimation of the contralateral breast because the subject was lying on that breast on the table during the imaging of the first breast. This causes the breast to warm and takes longer for steady state to be reached. A change in the design of the imaging table is presented to avoid this and ensure a shorter acclimation period by allowing both breasts to hang with a separating fabric that is used to obtain clear view of the breast being imaged.

Figures 3A, 3B, 3C:
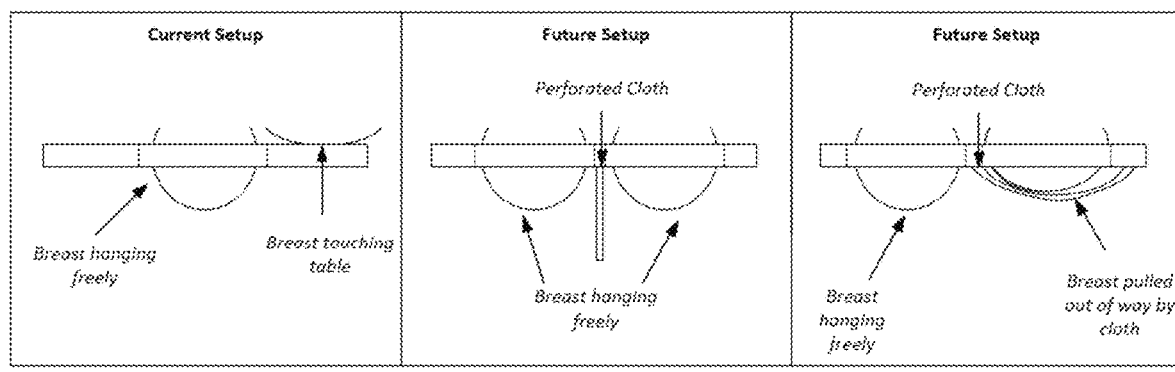
FIG. 3A shows a close-up schematic of the front view of the old table with the subject lying on one breast.
FIG. 3B shows the proposed future table with two holes and FIG. 3C shows the same table with one breast pulled aside with a perforated cloth.

In addition, the following techniques are disclosed to reduce the acclimation time. It is imperative with thermal imaging to observe the entirety of the breast surface and reduce any unwanted thermal alterations caused by the breasts touching each other or the breast touching the chest wall. The subject is imaged in the prone position, similar to an MRI. The original table design was meant to replicate tables used for stereotactic breast biopsy with one opening in the center to observe one breast at a time. However, the current table used for clinical imaging causes potential unwanted thermal alterations during imaging. The acclimation time needed to ensure steady state condition suitable for infrared imaging varies from 1 minute to twenty minutes. In some cases, a longer duration may be implemented. In an embodiment, all testing takes approximately 23 minutes. Changes in the protocols, imaging duration and intervals between images will cause changes in the total imaging time. The subject enters the room, disrobes from the waist up and places their right breast into the opening in the table while the left breast is tucked against the table. Ten minutes pass for proper acclimation and to ensure that the temperature on the breast reaches steady state. When the subject switches sides, the contralateral breast is significantly hotter. This requires a longer acclimation period to ensure that the temperature of the contralateral breast reaches steady state before imaging continues. Another embodiment of a clinical table for breast cancer screening is closer in design to a breast MRI table. Two holes are added, one for each breast, with a perforated cloth or a flexible fabric lying between them. The cloth is added to move one breast out of the way so the other breast can be imaged in a 360° view. In FIG. 3, the first panel shows the squished breast lying underneath the patient while the contralateral breast hangs freely through the opening in the table. This is found in the current clinical design, causing a longer acclimation and imaging period. The second panel shows the side view of a redesign with two holes cut in the table and the added cloth in between the two. The final panel shows the cloth is swept to the side to move the second breast out of the way. Although one breast will be touching a cloth, the perforations will prevent the breast from heating and will reduce acclimation time considerably.

Figure 4A:
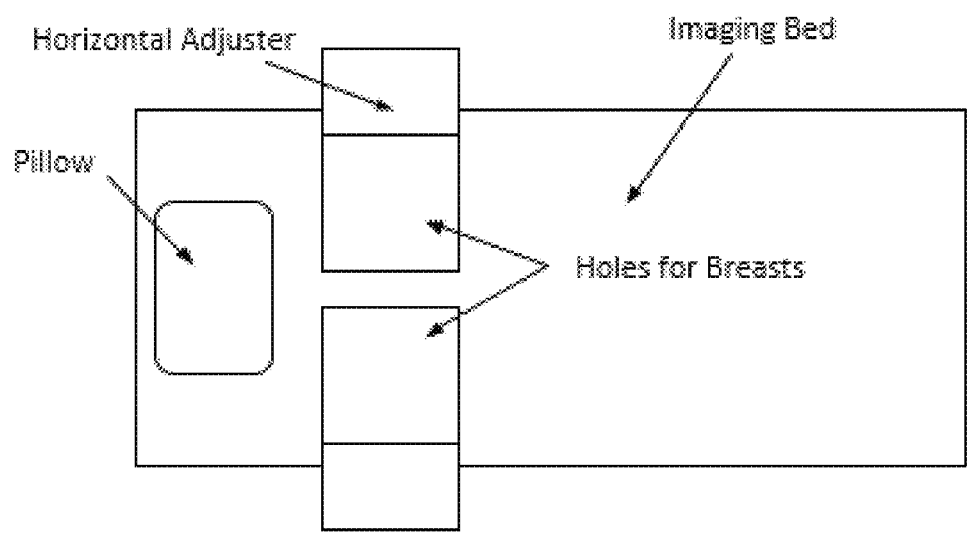
FIG. 4A shows a top view of a clinical bed with two holes and modular pieces to fit to each subject and FIG. 4B shows a bottom view of the bed with a subject lying on top.
Figure 4B:
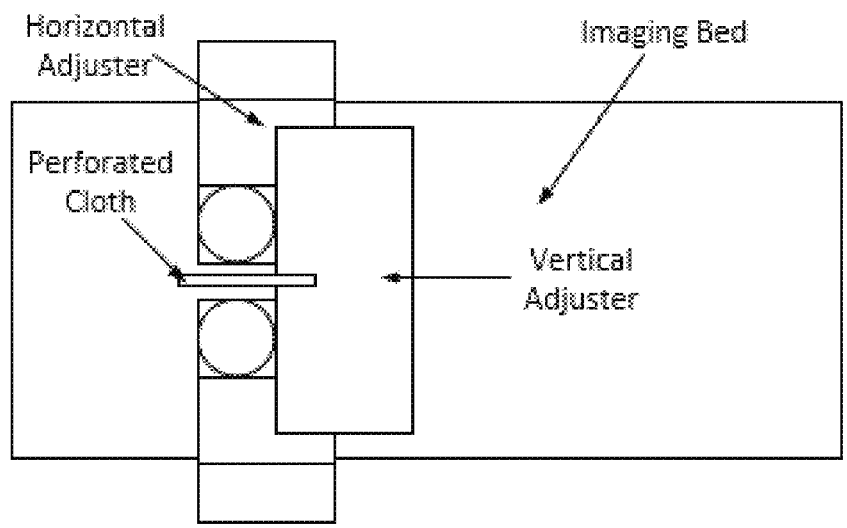

In addition to the added perforated cloth in between the two breasts, adjustable holes are added to fit to the patient. The table and the imaging system are designed to accommodate different ranges in breast size, shoulder width, body contour, and weight. In order to have one table that matches all patients, it can be made adjustable. A top view and bottom view of the new table with modular design is seen in FIG. 4.

There are modular pieces in the horizontal and vertical directions for each breast hole. When the subject lies on the table, the modular pieces will be adjusted to fit their breast size and weight. Once everything is adjusted accordingly, the perforated cloth will pull one breast to the side (FIG. 3C) and the acclimation period will begin. Extra padding will be added between the two modular holes to ensure subject comfort. The perforated cloth serves the function of pulling the non-imaged breast away so that clear access can be achieved for the IR camera. It needs to move the breast without causing significant thermal changes due to insulating effect. The perforations serve the purpose of providing air cooling while the breast is moved away. The perforated cloth may be replaced with a mesh, be made of different materials including wire, polyester, nylon, etc. Other potential modular designs could include a specially made gown for each patient with holes where the breasts lie and a larger slot within the imaging table. This would significantly reduce the influence of the chest wall on the resulting thermal images and would provide more comfort for the patient. Instead of altering the gown, a softer, cloth-made modular design could be implemented for the same purpose. Altering the clinical imaging table as opposed to the subject gowns will provide much more control and help with cleanliness.

Figure 5A:
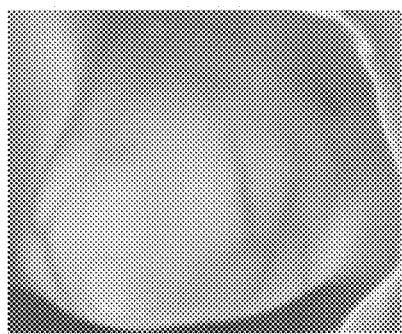
FIGS. 5A-5C show a series of images of the left Breast with Tumor of Patient 23, FIG. 5A two minutes into acclimation, FIG. 5B middle of acclimation time—5 minutes in, and FIG. 5C end of acclimation time—9 minutes later.
Figure 5B:
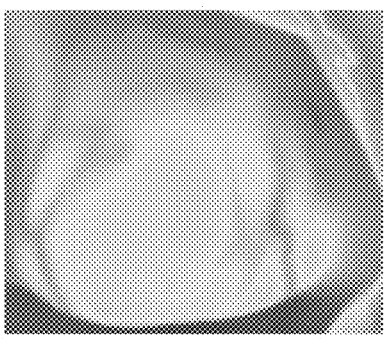
Figure 5C:
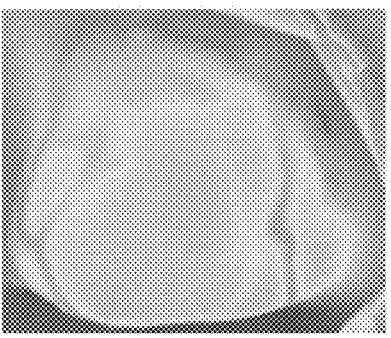
Figure 6:
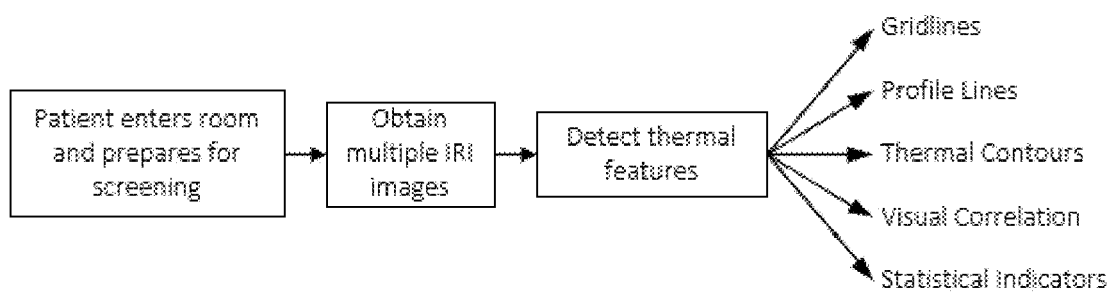
FIG. 6 is a flow chart of Method A to detect malignancy within tissue.
Figure 7:
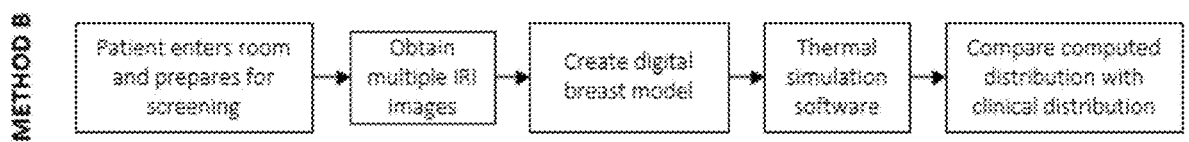
FIG. 7 is a flow chart of Method B to detect malignancy within tissue.
Figure 8:
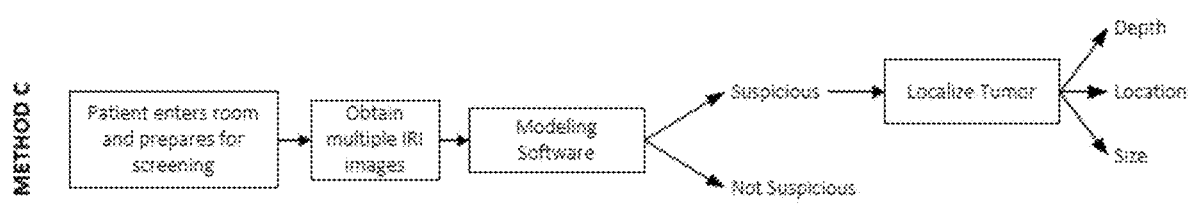
FIG. 8 is a flow chart of Method C to detect malignancy within tissue.
Figure 9:
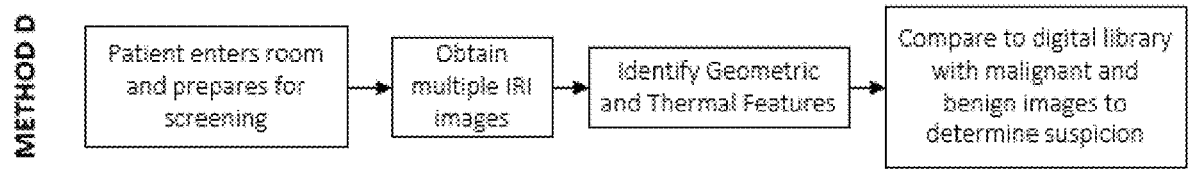
FIG. 9 is a flow chart of Method D to detect malignancy within tissue.

Acclimation Time—The desired acclimation time to reach steady-state is between 5 minutes and 20 minutes for efficient throughput with good imaging quality for accurate detection. A faster acclimation time may be reached by providing loosely fitting clothing or minimal clothing during wait period. The time used for the preliminary study was 10 minutes. The series of images in FIG. 5 shows the left breast, the breast without a tumor, of Patient 23. This patient had a lot of random vascular throughout the breast, some more striking or larger than other areas. The larger visible blood vessels running through the breast do not have a drastic temperature difference from the beginning of acclimation to the end. However, the smaller, deeper blood vessels do change over time and reflect differently on the surface. The change in acclimation time can change the visible thermal profiles on the breast surface, particularly where the blood vessels and tumor(s) are resting. One potential method of creating a more uniform temperature across the surface is by reducing the heat transfer rate from the breast to the environment. An insulating brassiere can be used to sit on the breasts for a certain amount of time to ensure even temperature is reached. When the bra is removed, the vasculature thermal profiles will change when exposed to ambient temperature. The resulting changes in vasculature temperature can be observed over a period of time. The observable cooling period for the breast once exposed to the ambient temperature can help in differentiating hot spots due to tumors vs. hot spots due to vasculature. Hot spots are also referred to as an area of increased hyperthermia. As the breast cools, the lines of vasculature become more defined and linear while the thermal regions induced by the tumor remain more diffuse. Some changes are expected when the tumor is closer to the skin surface and the intensity of the thermal changes is considered.

After the screening process, whether screening breast tissue or other body parts, one or more of the images are analyzed and it is determined whether or not a tumor is potentially present. The regions of interest are identified where thermal profiles are indicative of abnormalities that may be associated with the presence of cancer. The terms cancer and malignancy are used interchangeably and cover all forms of cancerous tissues. Different methods used to analyze thermal regions of interest are presented and discussed in greater detail in Method A. Method B describes the generation of a digital model of the body part using clinical images. A digital model is a 3D computer representation of the body part. The process can generate a 3D digital model of a body part whether the body part has a single tumor, multiple tumors or is considered healthy (free of suspicion). This model can be used to generate surface and internal temperature distributions of tissues using thermal simulation software (for example ANSYS Fluent). The generated temperature distributions can be compared with the temperature distributions in surface infrared images for the same orientation. The method also describes criteria that can be used to decide a match between the generated phantom thermal images and surface infrared images with actual temperature distributions. The thermal matching criteria are generated using Method A and are described further in Method C. Method C describes a technique to identify tumor characteristics including size, location, metabolic heat generation rate, and thermal properties of different components of the body part including, but not limited to tissues and fat layer. Method C can be used before or after suspected malignancy is detected. Method C employs the use of mathematical characterization of the temperature distributions, comparison of thermal images from the simulation and from the infrared images and a method to determine some or all of the thermal characteristics of tumor and healthy tissue.

Finally, images can be added to a digital library based on identified thermal and geometric identifiers to be used in further analysis and diagnosis, discussed in Method D. Similar procedures can be adapted for cancers of other body parts. If no regions of interest are identified, the patient may be referred back to a consulting radiologist or primary doctor. More details on the components of this patient workflow and the underlying mechanisms are described in greater detail below.

METHOD A: A method for determining malignancy within tissue using infrared imaging.—A region of interest is identified as a region on the body part surface where further analysis is considered based on the thermal abnormalities observed in surface infrared images. Tumors within tissue will have a greater amount of heat propagation throughout the tissue whereas vasculature or other thermally altering features will have a more defined thermal abnormality such as narrow and longer lines of increased temperature. After an image is taken, a geometric map is created on the surface infrared image using various techniques. There are multiple techniques that are used to develop a geometric map in order to detect regions of interest within tissue. These methods involve gridlines, profile lines, thermal contours, visual correlations and statistical indicators. Other mathematical or statistical parameters can be employed. Using the various techniques, thermal indicators are generated based on criteria specific to the technique used. Regions of interest are identified based on the thermal indicators and analyzed for suspected malignancy. Care is taken to avoid thermal saturation in the image over the tissue so that accurate information on temperature profile and its variation is obtained. Surface infrared images may or may not represent the exact surface temperature due to emissivity correction needed in the image. However, assuming the surface emissivity is uniform, the temperatures indicated by the infrared image are representative of the temperature field which may be somewhat offset from the true value. Use of lotion and other creams, etc. may cause changes in emissivity and their use is discouraged prior to imaging. The following techniques are used for analysis.

Statistical Indicators—There are several statistical indicators proposed in the techniques discussed below including but not limited to mean temperatures, minimum temperatures, maximum temperatures, standard deviation, variance, median, etc. in order to determine suspected malignancy. Qualitative and quantitative measures are derived based on the surface infrared image of the body part.

Correlate with Visual—Mastectomies, lumpectomies and other forms of scar tissue may create variations in thermal images or create confusing distortion. Combining IR imaging with visual data could help in determining if various thermal distortions should be examined more closely. However, obtaining visual images can be a sensitive issue from privacy considerations. Instead of digital photography, the tissue surface may be digitally reproduced using MRI images. Digital reproduction of a body part can be accomplished through other imaging modalities, including but not limited to, infrared imaging, outline capture techniques, shadow techniques, etc. In one embodiment, the imaging operator could write down observations about the visual scars, abnormalities, imperfects, etc. that correlate with factors seen in collected infrared images.

Temperature Distribution in a Thermal Grid—One such system of analysis would be the implementation of a grid along the body part. This grid could be sketched in multiple ways including a longitude-latitude type pattern with the longitudinal and latitudinal lines matching the contours of the body part. Other gridding systems could involve biased lines, changing line density based on features of focus or an alternate style of grid pattern. Although a few types of grids are described, any grid pattern that can be generated on the infrared image for further analysis or comparison will provide the needed information. The goal of implementing a grid is to enable defining the temperature variation in each segment of the body part. With an overall estimated average surface temperature, finding the variation in the mean temperature in each section of the body part can make it much easier to find abnormalities. Using a biased grid or a varying density grid can help for various purposes. It can also be used to single out various thermal abnormalities. Thermal abnormalities are defined as hot spots or regions of interest including but not limited to suspected malignancy, suspected benign masses, suspected vasculature or suspected scar tissue. With fewer grid boxes, it will be easier to find the boundaries of the thermal abnormality in order to determine if malignancy is a concern or if stray vasculature is creating additional heat signatures. The grid temperatures may be obtained as an average of one or more pixels at known locations in a grid that is mapped over the infrared image of the skin surface. Additional features such as elimination of outliers or similar procedures used in image processing may be applied.

Temperature profiles—Another method to identify thermal features is to obtain the surface temperature profile along lines drawn on the skin surface. These lines can be the same as described for the generation of the thermal grid. The temperature profile along these lines can be treated without processing, or processed to mitigate small temperature variations. Such processing can be done through Median, Average, Gaussian, Moving Average, Savitzky-Golay, Regression, or any combination of these filters. If the sign of the temperature gradient along the distance from the chest wall changes from positive to negative, it may be used as a marker of the presence of cancer. The distance over which the gradient is obtained is an important consideration. If the slope changes in certain region, while it may not change the sign, it may also be indicative of the cancer. If the slope changes by more than 10 percent over the certain distance, it may be used as a threshold. In other cases, a change from 10-50 percent or higher may be used as a marker. The slope is calculated over a reasonable distance to avoid any image aberrations. Thermal abnormalities can be classified as a temperature difference between maximum and minimum temperatures higher than 0.2° C. within a range of 2 mm to 10 mm, a preferred range of 2 mm to 5 mm. Thermal abnormalities are classified as a tumor if the temperature difference between maximum and minimum temperatures is higher than 0.5° C. over a 5 mm to 40 mm range, a preferred range of 10 mm to 30 mm. Thermal abnormalities are classified as veins if the temperature difference between maximum and minimum temperatures is between 0.2° C. and 2.0° C. over a 1 mm to 5 mm. If an abnormality is classified as both a vein and a tumor, it is classified as a tumor.

Aspect Ratios—In order to distinguish between possible tumors and blood vessels in a surface infrared image, the aspect ratio of the region of interest can be used. Tumors have a larger area of diffusion from the center of the hot spot to the surrounding tissue. Other factors such as veins have a more secluded, well-defined hot spot. By studying various lengths of hot spots on the skin surface, an aspect ratio can be calculated. This ratio, depending on the resulting value, will help indicate if an area is suspicious of malignancy or denotes a different thermal feature such as vasculature.

Thermal Contours—Using thermal contours with the hot spot in question as the central point is another method to hot spot differentiation and detection. Similar to a topographical map, thermal contours can be drawn around the hot spot and the diffusion through the tissue measured. Because of the increase in blood perfusion, malignant tumors have a stronger heat presence that steadily warms the surrounding areas, dissimilar to vasculature. Using appropriate markers, it is possible to identify the thermal changes due to angiogenesis. This may be a result of observing specific vasculature patterns that are noted in angiogenesis that are different from the regular vasculature. A comparison may also be made with infrared images obtained from prior visit or visits of the same subject to observe the thermal artifacts.

METHOD B: A method to generate a digital model and computer simulated temperature profiles on the skin surface of the body part from clinical images—A digital model is a digital entity that has the actual shape of the body part under analysis and can be manipulated and modified. Also, if necessary, a volumetric or surface mesh can be generated on the digital model. The digital model can be generated from any imaging or video modality of the body part under analysis, including but not limited to digital photographs, infrared images, magnetic resonance images, magnetic resonance angiograms, ultrasound images, mammograms either 2D or 3D, computed tomography scans, data from 3D scanners, laser scanners, depth sensors such as the Microsoft Kinect, video processing, or any combination of these and other imaging modalities. A tumor of known characteristics, including but not limited to size, shape, metabolic heat generation rate, and thermal properties of different tissue or fat can be introduced within the digital model. The digital model can be used to conduct computer simulations to compute temperature distributions or profiles for various tumor location and sizes. The resulting model, referred to as a phantom thermal model, is used for comparison with the surface infrared image. Appropriate thermal boundary conditions are employed in the thermal simulation, such as constant chest wall temperature, given heat transfer coefficient or coefficients on the skin surface, ambient temperature, and emissivity of the skin surface and temperature of surroundings if radiation effects are being considered.

The digital model can be generated from the data obtained from the imaging modalities or by processing one or multiple individual images using techniques such as image filtering, edge detection, segmentation, intensity transformation, multiview reconstruction, photogrammetry, marching cubes, marching tetrahedrons or any combination of these methods, or any other method that results in a 3D representation of the body part. If desired, the digital model can include the internal structures such as blood vessels and skin and fat layers. The resulting model can be used in its current state or modified to remove or add texture features either using a Computer Aided Design (CAD) software, a modeling software, or any software in which the model can me modified or smoothed to include new features. The digital model can include one or multiple tumors with characteristics including size, shape, location, metabolic activity, thermal conductivity, perfusion rate, etc.

Once the digital model contains the desired features, a mesh, either surface or volumetric, is generated in order to create smaller regions to solve the governing equations of heat transfer in the domain. The mesh can be generated by any software or procedure known in the art. The governing heat transfer equations can be solved using available commercial thermal simulation software or open source software. Preferably, the minimum number of mesh elements is 1,000 for volumetric meshes and 100 for surface meshes. A higher resolution can be achieved using at least 100,000 elements for volumetric and 5,000 for surface meshes. Higher or lower number of elements can be implemented depending on the size of the region and desired overall computation speed or accuracy. The quality of the elements in the resulting mesh should be within recommended values for the software for accurate numerical computations. For example, the skewness of the mesh elements should be below 0.95, with preferred values below 0.7. Depending on the sophistication of the software used, the actual number of mesh elements can be smaller or larger. Once the mesh is generated in the digital model, the governing equations can be defined. The governing equations can be analytical, empirical, semi-empirical or any combination thereof. Some examples are the Pennes Bioheat Equation, the Countercurrent, and the Jiji models. These governing equations may or may not take into account the effect of the vasculature on the temperature calculations. This effect can be included either using models for the vasculature, from clinical images or artificially generated using software such as Vascusynth. Appropriate values of the tissue properties and parameters should be defined prior to conducting the simulations, some of the parameters include thermal conductivity, specific heat, density, blood perfusion rate, metabolic activity, etc. The overall goal of the digital model and the thermal simulation is to provide an accurate estimation of temperature profile on the surface of interest for a given digital model with given tumor characteristics.

In order to solve the governing equations in the domain, either for a steady-state or transient formulations, boundary conditions are used to define the interactions of the computational domain with its environment. The surface is generally exposed to the still air, for which a convective boundary condition can be used. The value of the heat transfer coefficient considering a mixture of radiation, natural convection and evaporation from the skin is preferably in the range of 5-25 W/m$^2$-K; however any value can be used. Other alternatives include forced convection or natural convection by modeling the surroundings, a fixed initial surface temperature, radiation effects or any combination of these to account for the heat transfer between the model and its surroundings. For the other surfaces of the domain, any relevant boundary condition can be used, for example, fixed temperature, known heat flux, known temperature distribution, temperature distribution from experimental or analytical data, symmetry, insulated faces. These conditions can be either stationary or time dependent.

Once the digital model is meshed and the boundary conditions and tissue properties are set, the temperature field in the computational domain can be obtained from the thermal simulation software. The governing equation can be discretized in the software using the Finite Volume Method, the Finite Element Method, Finite Differences, The Boundary Element Method or any other suitable discretization method. The solution can be obtained using commercial software, open-access software, by developing in-house scripts/programs/algorithms, or any combinations of these. This software can run in parallel or serial mode either on a CPU or GPU (graphics processing unit). The solution can be obtained by running the routines in parallel, serial, multi-thread or single-thread processes in any architecture or processor, including, but not limited to CPU and GPU (graphics processing unit). Any other technique to obtain the thermal profile for a given digital model can be implemented.

The tumor introduced in the digital model can have any shape, including but not limited to spheres, cubes, ellipsoids, cylinders, pyramids, prisms, irregular shapes, actual tumor shape from imaging and any combination of those. The thermophysical properties of the tissues such as thermal conductivity, specific heat, blood perfusion, metabolic activity, or any other, can be constant, variable in space, variable in time, or any combination of these. The variation can be defined by any continuous, discontinuous or piecewise mathematical function or combination of functions. An optional but very highly recommended step is to validate the temperature computations of the digital model. In order to compute accurate temperature distributions, the predictions from the thermal simulation software should match closely to the temperature observed from the phantom thermal images to the surface infrared images. Therefore, it may be necessary to validate the digital model. Method B can be used to validate the digital model using a case where the tumor characteristics are known and the infrared images are available. The process steps in one such embodiment may be as follows—Obtain a digital model of the body part of interest from the infrared images or other imaging techniques. If available, incorporate the tumor characteristics in the digital model, generate simulated temperature distributions using thermal simulation software, compare the simulated and actual IR temperature distributions and determine whether there is a good match using thermal matching criteria.

In one embodiment, the phantom thermal images are generated using the thermal simulation software saved in views/orientations that reproduce the views/orientations that were used to capture the infrared images during clinical testing. To facilitate the comparison, the phantom thermal images and surface infrared images should correspond to the same view, orientation and angle of the body part. Image alignment also known as image registration or registration is an important step while comparing the phantom thermal image and surface infrared imaging in order to assure that the corresponding regions of interest are closely matched with each other.

The surface infrared images can be analyzed, either by technicians, clinicians, or through software either automated, semi-automated or manual, to inspect them for abnormal features, including but not limited to, abnormal lumps, scars, missing tissue and deformation. The outcome from the analysis can be used while comparing the computed and infrared images.

The validation can be conducted by comparing specific parameters in the computed and clinical thermal images at the pixel level (2D images), voxel level (3D images), or analyzing portions of the image or images, or the entire image or 3D model. The same or similar procedure can be used to compare images in other scenarios, such as comparing the results in an iterative procedure, outlined in Method C. The comparison is used to validate the digital breast model. It can also be used to verify the match between computed and infrared images, and update the values of the parameters in the iterative process.

In one embodiment, the portion or regions of the images to analyze can be a gridding system along the body part. The grid can be sketched as longitudinal and latitudinal lines following the contours of the body part, horizontal and vertical lines, skewed lines, concentric and eccentric lines and any other gridding system to divide the part under analysis. The grid lines can have a constant spacing or variable spacing. The region to be analyzed can be further divided into subdivisions, preferably more than 4 subdivisions. A more preferred number of subdivisions is more than 16.

In one embodiment, a central region representing between 1% and 100% of the image is used for comparison. In a preferred embodiment, a range between 5% and 75% is used, whereas, in a more preferred embodiment, a range between 25% and 50% is used. One of the factors in determining the range is the size of the region of interest, while other factors including, but not limited to, are size of image, registration match between the images.

These specific parameters can be individual indicators described in Method A, and including but not limited to mean, median, variance, standard deviation, texture, entropy, maximum, minimum, moment, correlation, or any other first or second order statistical parameter or mathematical function of them. The parameters can also be distributions of values along specific paths such as the gridding system proposed in this invention, along regions of interest in the images or 3D models, or a combination of these. It is preferred to conduct the comparison between parameters after the 3D models or individual images are aligned/registered to ensure that the comparison is being conducted between corresponding regions/levels, any suitable registration method such as intensity-based, feature-based or a combination of them can be used, although no image registration is required. During registration, images may or may not be scaled to the same size, although scaling is preferred to facilitate the comparison. The comparison of parameters can be conducted by computing the difference, absolute error, averaged error, mean squared error, correlation, any mathematical function between these or their combinations. The difference between the computed and clinical images in the thermal parameters that provide a representative temperature are called as the convergence criteria and should be below 3° C. for accurate tumor detection, but preferably below 1° C., or more preferably below 0.5° C., and most preferably below 0.2° C. The accepted value is balanced between the competing needs to reduce false positives and improve accurate detection. The convergence criteria could be based on other indicators such as temperature gradients, where differences between computed and actual should be below 3° C./cm, values below 0.5° C./cm are more preferred. Any other statistical parameter can be used to define the convergence criteria either thermal or in terms of pixel intensities of individual pixels or clusters of pixels from the images.

METHOD C: A method to localize a tumor within tissue—The digital model can be used in software to localize tumor in terms of estimating relevant parameters such as thermal conductivity of tissues (skin, fat, gland, muscle, tumor, etc.), blood perfusion and metabolic activity of the tissues, location, size and shape of a tumor, or external conditions such as ambient temperature, heat transfer coefficient, or any other relevant parameter. First, initial values of the parameters required in the digital model are set using thermal simulation software along with appropriate boundary conditions to generate phantom thermal images. The details of the digital model generation and thermal simulation described in Method B can be employed in Method C. The surface infrared images are the target images to which the generated phantom thermal images are compared. The phantom thermal images and surface infrared images are processed and compared using any criteria for comparison, such as described in Method B. If the difference of parameter values between the phantom thermal images and the surface infrared images is below a convergence criteria determined by the user, the values of the parameters are accepted as the estimates from the software. If the difference is above the convergence criteria, the parameters are updated and new phantom thermal images are generated, the process is repeated until the convergence criteria are satisfied and the parameter values are accepted. The comparison between the phantom thermal images and the surface infrared images can be done using any of the techniques and algorithms described in Method B. In order to update the values of the parameters to estimate, any optimization procedure can be used such as the Levenberg-Marquardt algorithm, The Gradient Descent method, The Conjugate Gradient Method, The Simulated Annealing Method, Particle Swarm Optimization, Ant Colony Optimization, Sequential Quadratic Programming, Artificial Neural Networks, Support Vector Machines, Genetic Algorithms, any combination of them and any other existing or new method suitable to solve optimization problems.

The localization of an area of suspected malignancy is defined as obtaining the location, size and other characteristics of a tumor. The location of the tumor can be measured in terms of a set of coordinates (x, y, z) from an origin to its center of gravity or to any other point inside the tumor outline or on its surface. Any coordinate system such as Cartesian, Cylindrical, Spherical, or any mapping and combination thereof can be used. Any combination and number of parameters can be estimated using the methods described herein. The estimation can be obtained from the phantom thermal images by comparing the thermal identifiers to a library of thermal identifiers. Other methods to conduct the estimation include Artificial Intelligence algorithms trained with data in the library of thermal identifiers including but not limited to Artificial Neural Networks, Support Vector Machines, Convolutional Neural Networks, Genetic Algorithms and any combination of these. Another method includes using a digital model prepared from any of the imaging modalities described herein.

The origin of the coordinate system to locate the tumor can be defined as any point either internal, on the surface, or external to any part of the body. The procedure can also be used to locate multiple tumors. The process for multiple tumor identification can be invoked when a single tumor has been identified and there is at least one region for which the clinical and computed temperature temperatures differ by more than 0.3° C., preferred values are above 1° C., more preferred values are above 1.5° C. The convergence criteria could be based on other indicators such as temperature gradients, where regions with differences above 0.5° C./cm are identified, values above 2.5° C./cm are more preferred. Higher or lower values of any of the convergence criteria could be employed to improve the detection accuracy. Any statistical indicator can be used to define criteria for multiple tumors, such as thermal indicators or indicators in terms of pixel intensities of individual pixels or clusters of pixels from the images. Thermal indicators refer to temperature changes on the body part surface observed in surface infrared images or phantom thermal images. Other suitable values may be used based on accuracy or speed of simulation, although accuracy is of primary concern. The location of the identified tumor is fixed and the procedure is repeated until a convergence criteria is met for the second tumor location and size. In case of more regions of discrepancy, the procedure can be repeated as many times as needed. If multiple tumors are present, an iterative procedure can be further implemented by keeping the second tumor fixed and refining the first tumor. Similar strategy can be used for multiple tumors. The process may be iteratively repeated to improve accuracy.

The estimated convergence criteria and parameters can be refined by comparing the outcome with clinical data, including surface infrared images. The parameters that can be refined include but are not limited to, tumor shape, aspect ratio, size, location, and other tumor characteristics to include early stages of cancer such as cell linings occurring in ductal carcinoma in situ.

One optional but highly recommended step is to analyze the outcome values of the estimated parameters, preferably those referring to the location and size of the tumor. The analysis can be done by trained personnel such as clinicians, for example the examining radiologist, or software, either automated, manual or semi-automated. The analysis can distinguish between different scenarios, including but not limited to tumor size and locations falling within common ranges for the specific cancer under analysis, tumor is not found in the domain under analysis or its location falls outside the domain, tumor is too small and its location is beyond common values, tumor is too big, etc. For each of the possible scenarios, the entity analyzing the outcome will provide recommendations for further analysis. The Method C is both applicable to steady state or dynamic infrared imaging.

METHOD D: A method to utilize a digital library for comparison—A digital library is generated from images such as clinical images, phantom thermal images, or surface infrared images of any body part in order to store relevant thermal and geometric data for future comparison with infrared imaging screening. The library is where information or data is stored in electronic or other media forms. When images of a body part are added to the digital library, geometric and thermal identifiers are identified. The geometric identifiers of images of a body part are compared with the geometric identifiers of images found in the digital library. After a geometrically similar match is identified, the thermal identifiers are compared. The digital library may contain geometric identifiers, thermal identifiers, and infrared images from different orientations and distances, patient details, tumor identifiers including size, shape and histology, details regarding how the information was obtained, computer generated thermal images and their geometric identifiers, thermal identifiers and tumor identifiers. The geometric identifiers are identifiers that are related to the geometrical details of the body part. These libraries can be dynamic and trained with individual case studies. The tumor identifier may include information regarding whether a tumor is present or not, its size, shape, type of tumor and other tumor location details that enable location of the tumor within tissue. The thermal identifiers may include information on the tumor properties and how they affect the surface temperature profile. They may include information on maximum temperatures, minimum temperatures and the gradient throughout the tissue.

In accordance with an aspect of the present disclosure, there is provided a breast cancer detection process using infrared images in which geometric and thermal identifiers are generated and compared with identifiers stored in a digital library to determine tumor characteristics.

In an embodiment, a method for breast cancer detection includes:
  a. isolating the breast and obtaining thermal images using an infrared camera;
  b. comparing images to those in the digital library for geometrical identifiers including,
     looking for similarities in geometry, including but not limited to breast shape, breast size, breast circumference, distance from chest wall to nipple, volume, etc;
  c. comparing images to geometrically similar images in digital library for thermal identifiers including,
     utilizing thermal identification methods including but not limited to thermal contours, thermal profiles, statistical indicators, and gridlines;
  d. using thermal indicators to determine abnormality; and
  e. adding thermal images to digital library for future comparison.

In accordance with an aspect of the present disclosure, there is provided a procedure to obtain clinical infrared images of the isolated breasts from multiple positions including:
  a. subjects either with or without breast cancer are recruited;
  b. subjects asked a series of questions about potential activities and factors that can influence thermal distribution of the breast;
  c. one breast is isolated and allowed to acclimate to room temperature;
  d. multiple images are taken around the circumference of the breast; and
  e. the process is repeated for the contralateral breast.

In accordance with an aspect of the present disclosure, there is provided a procedure to generate geometric identifiers of the breast that contain relevant geometric information to define the shape, structure and topology of the breasts:
  a. isolating the breast and obtaining clinical images of multiple views including,
     clinical images obtained using methods including but not limited to infrared imaging, MRI, mammogram and x-ray;
  b. generating a 3D digital model using collected images;
  c. measuring multiple factors on the breast including but not limited to the circumference around the breast at multiple locations, the distance from the nipple to the chest wall, the size of the breast, the shape of the breast, horizontal and vertical dimensions of breast, etc.; and
  d. adding images to digital library for future comparison.

In accordance with an aspect of the present disclosure, there is provided a procedure to generate thermal identifiers to identify regions of increased hyperthermia obtained from surface temperature information of a body part:
  a. multiple methods are used during post-processing to identify regions of interest and differentiate between vasculature and tumors, including but not limited to,
     i. gridlines including,
        1. gridlines including latitude and longitude drawn on the body part creating individual boxed regions on the body part,
        2. average temperature in each box calculated,
        3. temperatures differences between adjacent boxes greater than 0.3° C. are considered suspicious,
        4. additional lines drawn closer together in areas of increased hyperthermia to narrow region of interest,
        5. tumors or veins identified using increased areas of hyperthermia also known as hot spots, and
        6. veins and tumors differentiated,
     ii. profile lines including,
        1. lines drawn through regions of identified interest also known as regions of increased hyperthermia,
        2. the plots created correspond to temperature changes over distance along the profile lines,
        3. slope of the resulting plot lines measured and identified as abnormalities or normal thermal changes,
        4. thermal abnormalities are classified as a temperature difference between maximum and minimum temperatures higher than 0.2° C. within a range of 2 mm to 10 mm, a preferred range of 2 mm to 5 mm including,
           i. thermal abnormalities are classified as a tumor if the temperature difference between maximum and minimum temperatures is higher than 0.5° C. over a 5 mm to 40 mm range, a preferred range of 10 mm to 30 mm,
           ii. thermal abnormalities are classified as veins if the temperature difference between maximum and minimum temperatures is between 0.2° C. and 2.0° C. over a 1 mm to 5 mm, iii. if an abnormality is classified as both a vein and a tumor, it is classified as a tumor,
iii. contours including,
1. contours drawn around visible hot spots or temperature differences,
2. heightened temperatures detected and identified as abnormalities,
3. aspect ratios used to define regions of interest and differentiate veins and tumors; and
b. abnormalities detected by gridding systems and profile lines are classified as thermal identifiers and added to digital library for future comparison.

In accordance with an aspect of the present disclosure, there is provided a breast cancer detection process using infrared images and thermal images generated through numerical simulations in which a matching algorithm is used to determine the tumor characteristics:
a. isolating the breast and obtain thermal images using an infrared camera;
b. storing the individual images with image identifiers, including patient data, orientation of the camera and patient, geometrical identifiers;
c. generating digital breast model;
d. generating thermal images of the breast surface including,
  i. the digital model and initial tumor characteristics,
  ii. thermal simulation software. Alternatively, artificial intelligence algorithms including but not limited to neural networks and support vector machines can be used to generate the surface the temperature distributions; and
e. using matching algorithm to determine tumor characteristics.

In accordance with an aspect of the present disclosure, there is provided a procedure to generate a digital breast model from clinical or optical images of the breasts:
a. a process to generate digital breast models from images including, but not limited to digital photographs, infrared images, MRI images, ultrasound images, Mammograms, either 2D or 3D, computed tomography scans, 3D scanners, laser scanners, depth sensors such as the Microsoft Kinect or any other, any other imaging modality or video capture from which the breast outline can be obtained;
b. the digital breast model can be generated from the data obtained from the imaging modalities or by processing one or multiple individual images using techniques such as image filtering, edge detection, segmentation, intensity transformation, multiview reconstruction, photogrametry, marching cubes, marching tetrahedrons or any combination of these methods, or any other method that results in a 3D representation of the breast. If desired, the digital breast model can include the internal breast structure such as lobules, blood vessels and milk ducts, where available. The resulting breast model can be used in its current state or modified to remove or add texture features either using a Computer Aided Design (CAD) software, a modeling software, or any software in which the model can me modified or smoothed to include new features;
c. collected clinical images are formed into a 3D model through image analysis;
one of the embodiments of image combination includes the following,
  1. remove artifacts in MRI images,
  2. segment the breast in the MRI images,
  3. images are stacked and a model is formed, and
  4. model is smoothed to create seamless digital model of actual breast shape.

In accordance with an aspect of the present disclosure, there is provided a procedure to generate thermal images using a digital breast model:
a. using digital model generated from clinical images;
b. a mesh to divide the computational domain. The mesh can be generated by any software or procedure. It is desired that the minimum number of mesh elements is 1000 for volumetric meshes and 100 for surface meshes. A better resolution can be achieved using at least 100000 elements for volumetric and at least 5000 for surface meshes. The quality of the elements in the resulting mesh must be within recommended values for accurate numerical computations. For example, the skewness of the mesh elements must be below 0.95, with preferred values below 0.7. Depending on the sophistication of the software used, the actual number of mesh elements can be smaller or larger;
c. defining the governing equation for heat transfer in tissues. The governing equations can be analytical, empirical, semi-empirical or any combination and any number of these. Some examples are the Pennes Bio-heat Equation, the Countercurrent, and the Jiji models. These governing equations may or may not take into account the effect of the vasculature on the temperature calculations. This effect can be included either using models for the vasculature, from clinical images or artificially generated using software such as Vascusynth;
d. defining values of properties of the tissue and other thermal and biological factors; and
e. defining boundary conditions. The surface of the breast is generally exposed to the still air, for which a convective boundary condition can be used. The value of the heat transfer coefficient considering a mixture of radiation, natural convection and evaporation from the skin is typically in the range of 5-25 $W/m^2$-K; however any value can be used. Other alternative is to include forced convection or natural convection by modeling the surroundings of the breast, a fixed initial surface temperature, radiation effects or any combination of these to account for the heat transfer between the model and its surroundings. For the other surfaces of the domain, any relevant boundary condition can be used, including but not limited to, fixed temperature, known heat flux, known temperature distribution, temperature distribution from experimental or analytical data, symmetry, insulated faces. These conditions can be either stationary or time dependent.

In accordance with an aspect of the present disclosure, there is provided a procedure to utilize matching algorithm to determine tumor characteristics:
a. isolating the breast and obtain thermal images using an infrared camera;
b. generating digital breast model;
c. inputting tumor parameters, including but not limited to size, location, shape, aspect ratio, metabolic activity, blood perfusion. These values can be obtained from clinical images, patient data, or can be guessed as an initial value in an iterative procedure;
d. generating thermal images of the breast surface using,
  i. a digital model and initial tumor characteristics,
  ii. thermal simulation software, alternatively, artificial intelligence algorithms including but not limited to neural networks and support vector machines can be used;

e. selecting the region to be analyzed in the images and compute thermal identifiers. The thermal identifiers may include information on the tumor properties and how they affect the surface temperature profile. The thermal identifiers are used to characterize the thermal distribution and include but are not limited to information on maximum temperatures, minimum temperatures and the gradient throughout the tissue. The region to be analyzed can be further divided into subdivisions;
f. comparing the infrared and computed thermal images using a cost function including but not limited to error, mean squared error, correlation, cross-entropy. The cost function is any mathematical function to measure discrepancies between the IR and computed thermal images;
g. updating the value of the tumor characteristics in an iterative procedure using optimization methods including but not limited to, Levenberg-Marquardt, Gradient Descent, Newton, Steepest Descent, Particle Swarm Optimization, Simulated Annealing Method, Genetic Algorithms, Sequential Quadratic Programming;
h. continuing the method until cost function is below a predetermined threshold; and
i. identifying the estimated tumor characteristics as the outcome from the algorithm.

In accordance with an aspect of the present disclosure, there is provided a procedure to utilize wireless technology for remote, portable infrared imaging to identify suspected malignancy:
a. portable infrared imaging camera is used in specific orientations including but not limited to frontal, oblique views, downward looking, upward looking on the body part being imaged;
b. transmitting these images to a processing center for further evaluation;
c. images are processed using techniques described in Method A—Method D to identify suspected malignancy;
d. further actions will be taken for further evaluation including,
 i. doctors consulted, and
 ii. further imaging including but not limited to x-ray, mammography, IRI detection, ultrasound, MRI, CT scan, physical examination, etc.

In accordance with an aspect of the present disclosure, there is provided a procedure to monitor the usage and efficacy of chemotherapy and/or radiation for progression of treatment:
a. chemotherapy drugs or radiation is induced into the growing tumor to shrink the mass;
b. cancer patients receive periodic infrared screening to observe the tumor's activity including,
 i. as treatment is given, the tumor should begin to shrink and its metabolic activity should reduce,
 ii. if shrinkage not observed, treatment may be ineffective; and
c. discuss outcome with consulting physician and alter treatment accordingly.

The disclosure will be further illustrated with reference to the following specific examples. It is understood that these examples are given by way of illustration and are not meant to limit the disclosure or the claims to follow.

Example 1, Method A

Figure 10A:
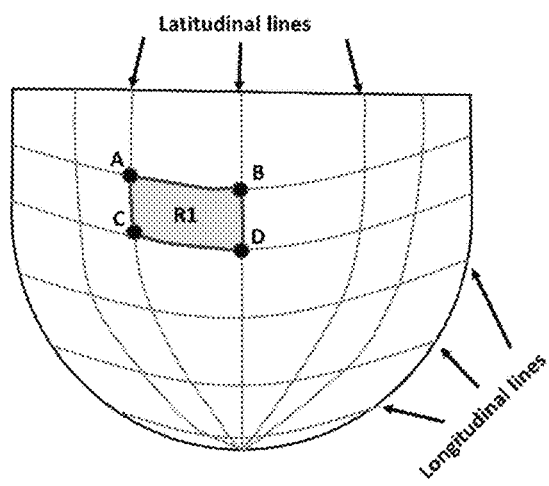
FIG. 10A is an example of a grid having latitudinal and longitudinal lines and FIG. 10B is an example of a grid having horizontal and vertical lines.
Figure 10B:
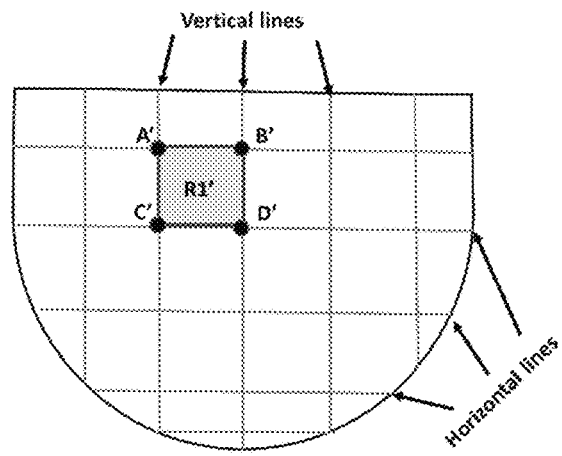
Figure 11A:
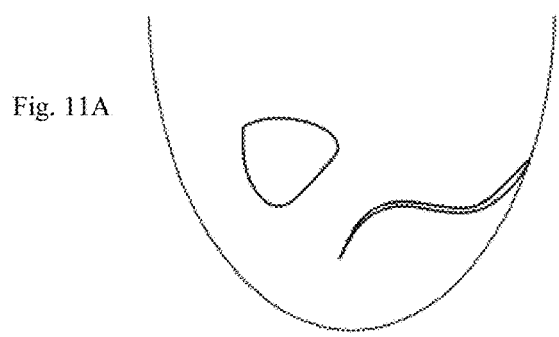
FIG. 11A is a breast with tumor hot spot and vein hot spot.
Figure 11B:
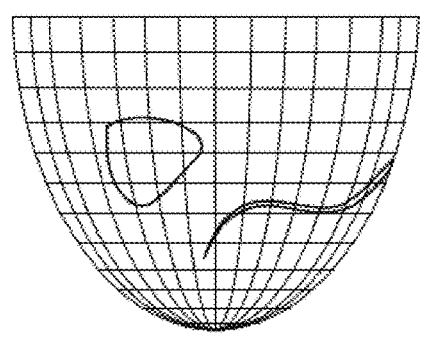
FIG. 11B is a gridding system on breast.
Figure 11C:
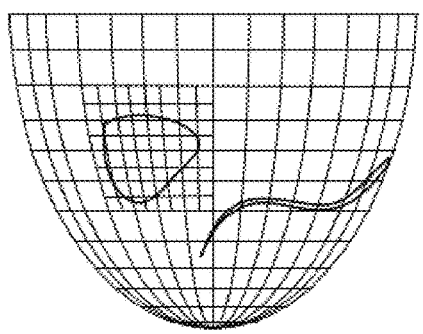
FIG. 11C is a refined mesh highlighting tumor hot spot and FIG. 11D is a refined mesh highlighting vein hot spot.
Figure 11D:
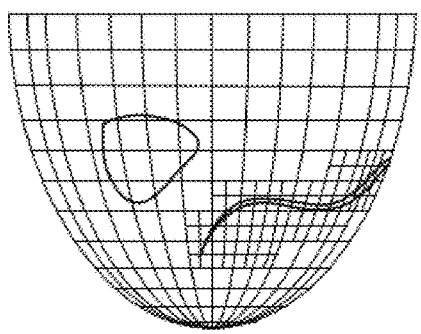

One example of varying gridline patterns can be seen in FIG. 10. In FIG. 10A the grid is composed by latitudinal lines (parallels) and longitudinal lines (meridians) that match the contours of the breast; this grid is similar to the coordinate system used to locate points on the Earth surface. The grid shown in FIG. 10B is composed of horizontal and vertical, similar to a Cartesian coordinate system. The grid can also be composed of oblique lines, circular segments, hyperbolic, parabolic lines, functions resulting from statistical fitting (quadratic, cubic, exponential, logarithmic, linear, etc.), or any combination of these. They can be matched on the breast outline. The points where the two types of lines intersect define the nodes of the grid. These nodes (for example A, B, C and D in FIG. 10A or A', B', C' and D' in FIG. 10B) define the regions (R1 or R1') where the quantities of interest will be obtained.

Example 2, Method A

Another example gridding system, seen in FIG. 11, can show the importance of a finer mesh. The hot spot resulting from the tumor is on the left side of the breast and the hot spot resulting from a vein is on the right side of the breast. The grid system is drawn over the breast surface with horizontal (latitude) and vertical (longitude) lines. When a region of interest is identified, a finer meshing system is applied. The average temperature value in each square can be found to determine the significance of the hot spot. With a finer grid in specified regions of interest, the average temperature values will change. The temperatures at the hot spot will be significantly hotter than the surrounding tissue. Using a grid system can help identify potential regions of concern as well as differentiate between a tumor and a vein.

Example 3, Method A

As an example, the mean (Tmean), maximum (Tmax) and minimum (Tmin) temperatures and standard deviation (SD) were computed in the regions shown in FIG. 12A. The statistical parameters are shown only in six regions to illustrate the advantages of using the thermal grid. In order to conduct a complete analysis, all regions should be analyzed. In addition to such statistical parameters, other indicators include entropy, energy, histogram analysis, texture, variance, correlation, contrast, skew, kurtosis and any combination or product of these. FIG. 12B shows the values of these parameters. Region 1 is expected to have a high mean temperature relative to other regions; besides the temperature range is only 0.5° C. Region 2 is expected to have a mean temperature lower than Region 1; however, the mean temperature is 1.7° C. higher than Region 1. The temperature range in Region 2 is 2.7° C. and the standard deviation is high, which indicates that a possible abnormality is found near Region 2. Region 3 also presents an elevated temperature with a range of 1° C. Regions 4 and 5 present lower and more uniform temperatures than Regions 2 and 3. From the previous analysis, the possible abnormality is located in the vicinity of Regions 2 and 3. The density of lines can be increased in such Regions to aid in the identification of abnormal temperatures. With fewer grid boxes, it will be easier to find the boundaries of the thermal abnormality in order to determine if malignancy is a concern or if stray vasculature is creating additional heat signatures.

Although an example of the grid pattern is presented above, any other type of grid pattern, and temperature calculations based on the temperature of the nodes, several pixels around nodes, or different regions identified by the grid patterns can be used to arrive at the thermal markers. The temperature elevation in a region over an unaffected region may be 3° C. or higher for aggressive tumor, or tumor close to the surface, 1-3° C. for the smaller tumor or deep inside, or between 0.1 to 1° C. for very small or very deep tumors. The small and large are somewhat qualitative, generally small meaning less than 7 mm, medium being between 0.7-2 cm and large being greater than 2 cm. These boundaries are not fixed and may be changed depending on the individual case depending on the breast size. Tumor depths are also somewhat subjective and may be indicative of near surface, around within 10 mm, or moderate around 10 mm to 20 mm, and deep beyond these values. These are also subject to variation depending on tumor location, breast size, etc., similar to other classification presented earlier and vice versa.

Example 4, Method A

Figure 13:
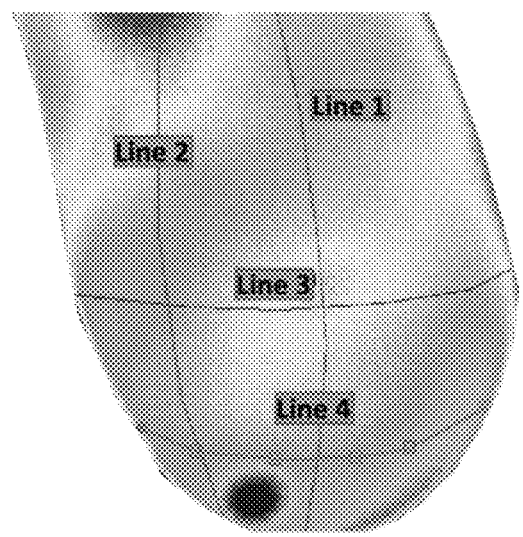
FIG. 13 is a breast infrared image of an individual with breast cancer showing selected lines to report temperature profiles.
Figure 14A:
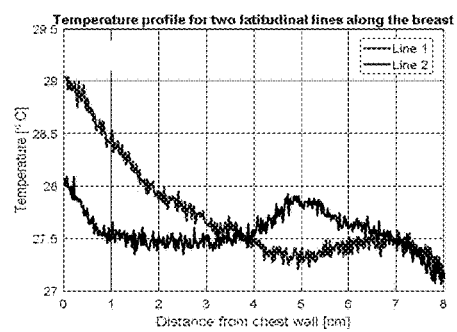
FIG. 14A is a temperature profile along the selected Lines 1 and 2.
Figure 14B:
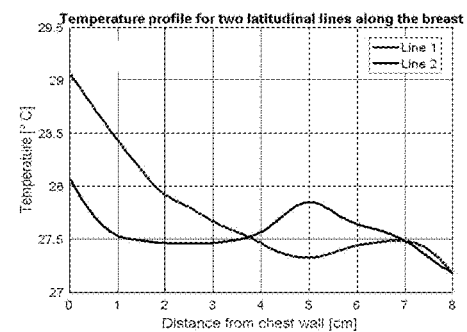
FIG. 14B shows smoothed profiles.
Figure 14C:
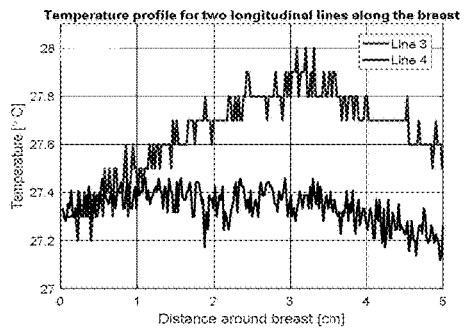
FIG. 14C is a temperature profile along the selected Lines 3 and 4.
Figure 14D:
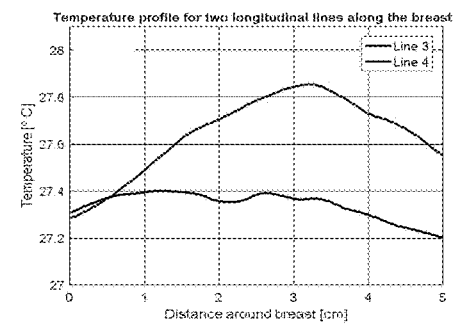
FIG. 14D shows smoothed profiles.

FIG. 13 shows the breast thermogram of an individual with breast cancer. Lines 1 and 2 are latitudinal lines, Lines 3 and 4 are longitudinal lines. FIG. 14A shows the temperature profile for Lines 1 and 2, the filtered profiles for these lines are shown in FIG. 14B. The temperature of Line 1 starts from ~28° C. near the chest wall and decreases. After 1 cm, the profile flattens and shows a peak at around 5 cm; the temperature rise is ~0.5° C. with respect to the surrounding temperatures, which helps locate possible malignancy. The profile of Line 2 decreases from its maximum near the chest wall to its minimum at the tip of the breast. This profile does indicate that no abnormality is observed along Line 2. FIG. 14C shows the temperature profile for Lines 3 and 4, the filtered profiles for these lines are shown in FIG. 14D. The temperature along Line 3 increases continually and then decreases near 3 cm. This change in slope (temperature gradient) indicates the presence of an abnormality. The temperature of Line 4 is almost uniform with only slight variations, which indicates that no abnormalities are observed along Line 4. In the previous example, the temperature of Line 1 starts from ~28° C. near the chest wall and decreases. After 1 cm, the profile flattens and shows a peak at around 5 cm. The temperature rise is ~0.5° C. with respect to the surrounding temperatures, which indicates possible malignancy. The profile of Line 2 decreases from its maximum near the chest wall to its minimum at the tip of the breast. This profile indicates that no abnormality is observed along Line 4.

Example 5, Method A

Figure 15:
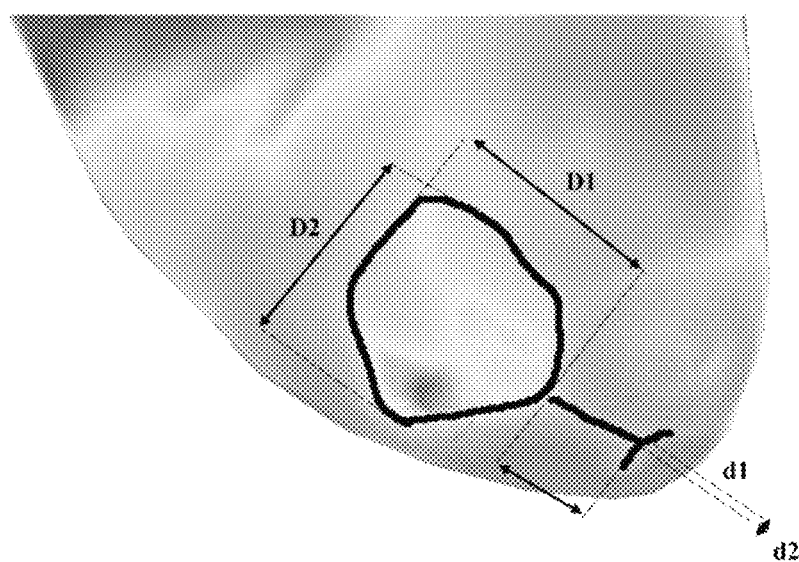
FIG. 15 is an IR image of a breast with tumor showing two regions of interest.

Both tumors and blood vessels cause local temperature rises. The aspect ratio D1/D2, where L1, the largest dimension, is close to one which indicates that the abnormality is likely caused by a tumor. The aspect ratio for possible tumors can be from 1 to 4. This value may be larger if the tumor is large, which will show up as wider regions in the normal direction, while the blood vessels will not generally be wider than about 5 mm or 7 mm. The aspect ratio d1/d2 is ~15, which indicates that this is likely caused by a blood vessel. Aspect ratios larger than five (5) are indicative of blood vessels. In some cases, these values may be further refined based on the actual width of the enhanced thermal region since tumors would be wider while the blood vessels would be narrower. This needs to be further evaluated with consideration of DCIS which may present a somewhat similar to the effects of blood vessels. These results correlate with the tumor location obtained from the MRI images and the surface blood vessels from the MRI rendering shown in FIG. 15 for Subject 6.

Figure 16:
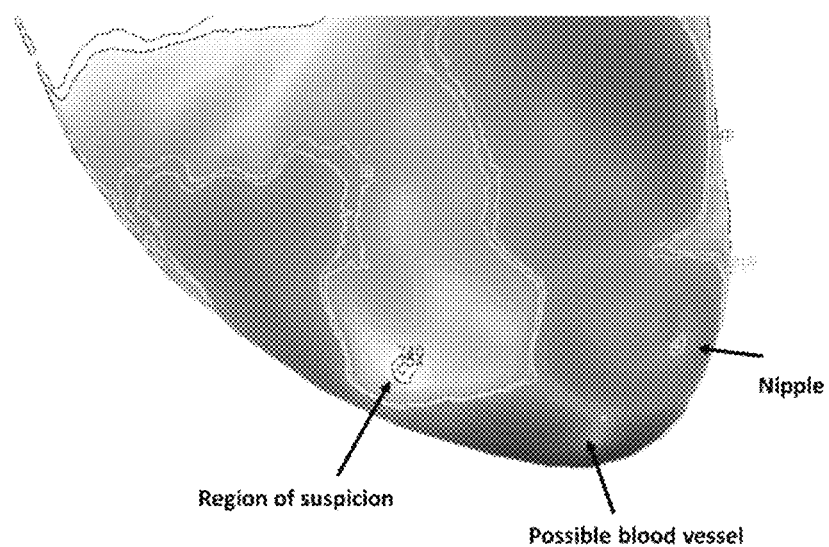
FIG. 16 shows temperature contours on a breast thermogram of an individual with breast cancer.

FIG. 16 shows temperature contours for the same subject. These temperature contours are warmer (red), more circular and closed in the region surrounding the tumor. In the region surrounding the blood vessel of interest, the contours have higher aspect ratios and are colder than for the region surrounding the tumor, which shows the potential of temperature contours to distinguish between possible tumors and blood vessels from infrared images. Thermal contours are also effective thermal markers of the cancer. If the contour plots show concentric regions that are indicative of steep hill type feature, the region may be a suspect. If the gradient in this region is high as discussed earlier, then it can be used as a further marker.

Example 6, Method B

Figure 17:
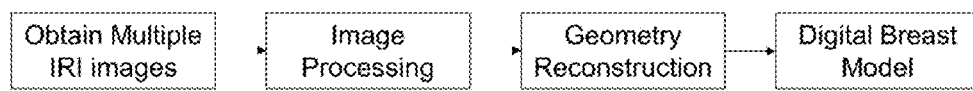
FIG. 17 is a flow chart of a procedure to generate a digital breast model from IRI images.

A digital breast model was generated from MRI images of the breast and it was used to generate and validate temperature distributions with clinical images. A succinct flowchart of the digital model process is seen in FIG. 17.

The MRI study, consisted of 178 images, the region containing the breast of interest was selected. Then, the tumor was measured and its location was stored for future steps. The tumor was modeled as a sphere with a diameter of 2.7 cm. A 3D median filter was applied, the dimensions of the applied 3D median filter were (3, 3, 3). The outline of the breast was detected using a modified version of the Canny edge detector, which detected a continuous outline of the breast. Then, the breast was segmented by defining everything inside the breast outline as breast tissue and the region outside as the background. The breast surface was generated from the stack of MRI slices using the Marching Cubes algorithm, which results in a surface mesh composed of triangular elements. The resulting surface mesh was jagged and needed to be smoothed to represent more accurately the geometry of the breast. The surface mesh was smoothed using an algorithm that replaced the angle of a mesh face with the average angle of the neighboring faces; which is similar to applying an averaging filter to a 3D image. In the smoothed breast geometry, some regions of the mesh were further smoothed using the software Autodesk Recap Photo only on the regions that needed it. The resulting surface mesh is seamless and accurate.

Figure 18:
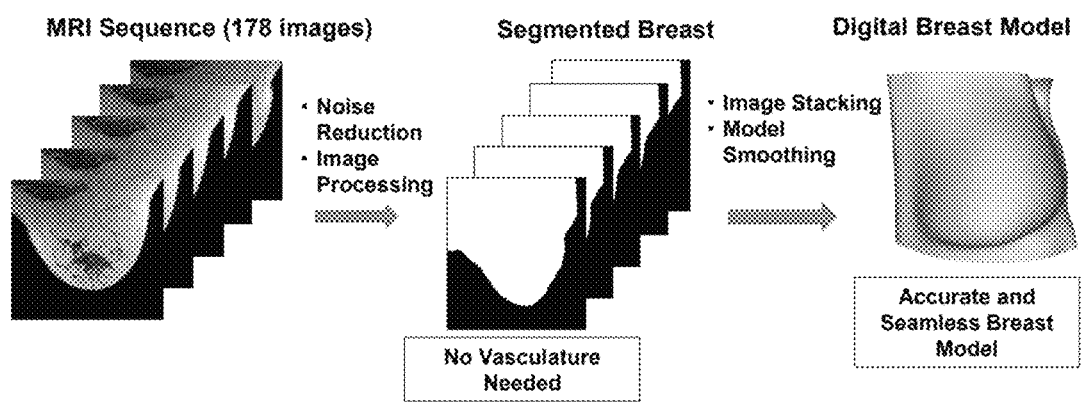
FIG. 18 illustrates results of geometry reconstruction for a test case.

The generated digital breast model is shown in FIG. 18. This model was used to compute the surface temperature.

Figure 19:
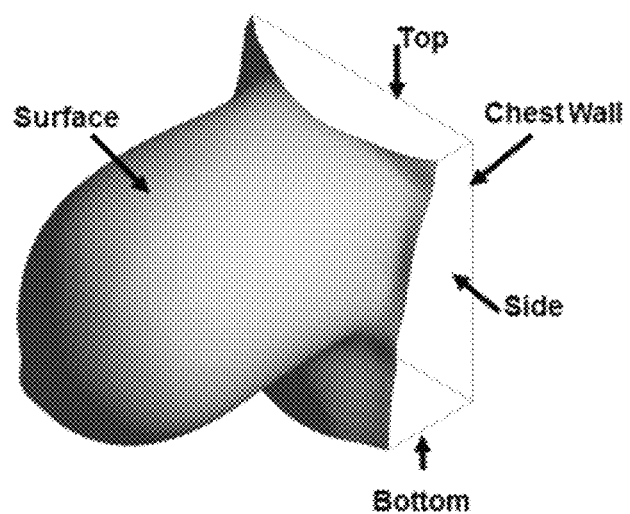
FIG. 19 shows the computational domain used to compute the temperature distribution.

The commercial software ANSYS Fluent was used to predict the breast surface temperature profile. The solution is based on solving the underlying heat transfer equations with convective blood flow. The Pennes' bioheat equation was used to account for the thermal interactions occurring within the breasts and in the environment. Pennes' equation is given by:

$$\rho_t c_t \left(\frac{\partial T_t}{\partial t}\right) = \nabla \cdot (k_t \nabla T_t) + \omega_b c_b (T_a - T_t) + q_m \qquad (1)$$

where $\rho$, c and k are the density, specific heat and thermal conductivity, respectively. The subscripts t, b and a refer to tissue, blood and arteries, respectively, $\omega$ is the blood flow rate per unit tissue volume (perfusion rate in kg/m$^3$-s) and $q_m$ is the metabolic activity within the tissue in W/m$^3$. The computational domain used to compute the temperature distribution is shown in FIG. 19. The breast surfaces are subjected to a convection boundary condition, where values of the ambient temperature and heat transfer coefficient can be reasonably well estimated and entered in the software. The chest wall is considered to be at the core temperature of the body.

To take into consideration the two blood perfusion and metabolic activity terms in the Pennes equation, these terms were defined as source terms in the software using User Defined Functions (UDFs). The UDFs were prepared to vary the location and size of the tumor without need to again mesh the tumor domain separately. This offers flexibility if the position and size of the tumor is changed in the model because there is no need to re-mesh the domain; only the UDF will be modified to account for the new tumor position and size.

TABLE 1

Values of the parameters used to compute the thermal images.

| Parameter | Value | Unit |
| --- | --- | --- |
| Thermal conductivity (k) | 0.42 | W m$^{-1}$ K$^{-1}$ |
| Perfusion rate of healthy tissue ($\omega_h$) | 1.8 × 10$^{-4}$ | s$^{-1}$ |
| Perfusion rate of tumor ($\omega_t$) | 9 × 10$^{-3}$ | s$^{-1}$ |
| Metabolic activity of healthy tissue ($q_h$) | 450 | W m$^{-3}$ |
| Metabolic activity of tumor ($q_t$) | 6350 | W m$^{-3}$ |
| Temperature of arteries ($T_a$) | 37 | ° C. |
| Specific heat of blood ($C_b$) | 3,840 | J kg$^{-1}$ K$^{-1}$ |
| Density of blood ($\rho_b$) | 1,060 | Kg m$^{-3}$ |
| Core temperature ($T_c$) | 37 | ° C. |
| Ambient temperature ($T_\infty$) | 21 | ° C. |
| Heat transfer coefficient | 10.5 | W m$^{-2}$ K$^{-1}$ |

Figure 20:
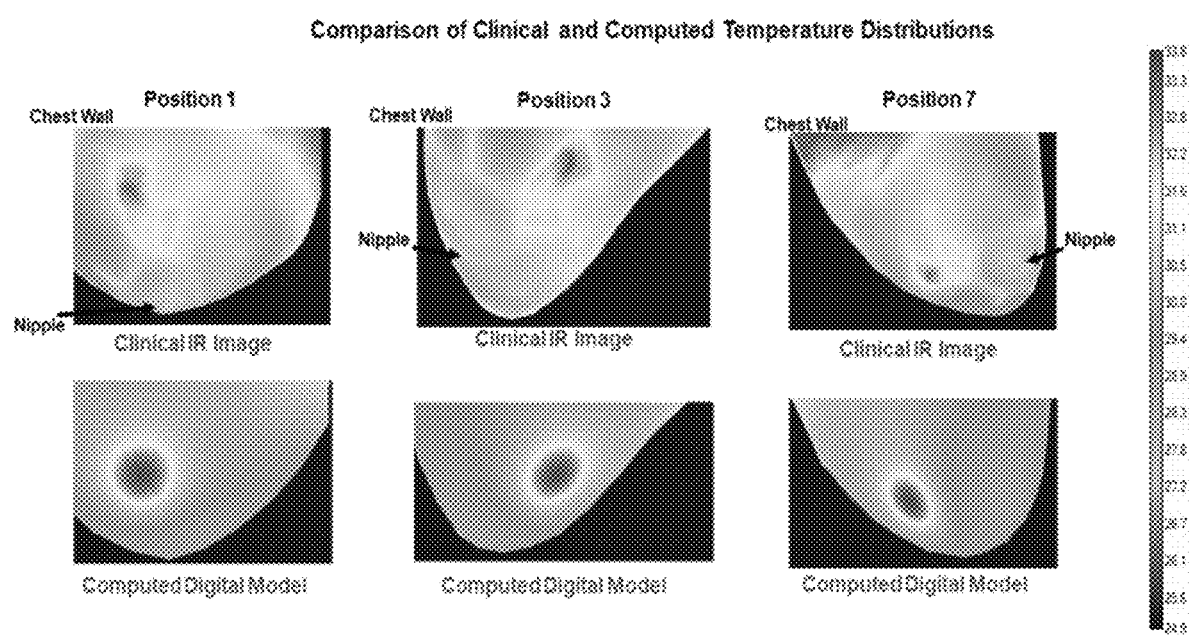
FIG. 20 is a comparison of a series of clinical and computed thermal images.
Figure 21:
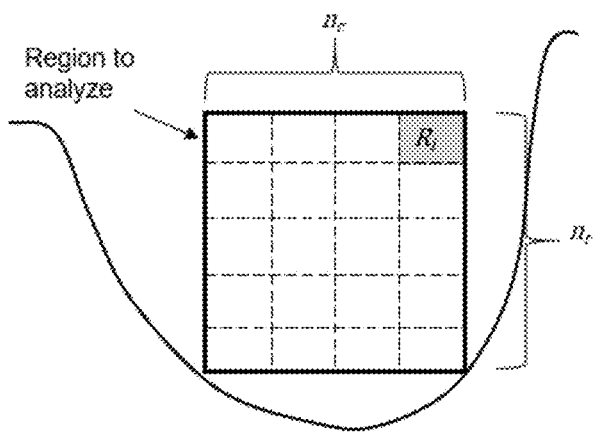
FIG. 21 is a schematic of a region to analyze in clinical and computed thermal images.
Figure 22:
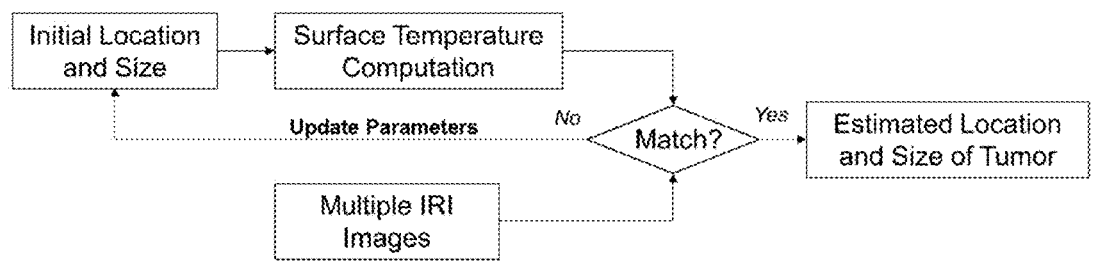
FIG. 22 is a flow chart of an iterative algorithm to estimate tumor parameters from thermal images.
Figure 23:
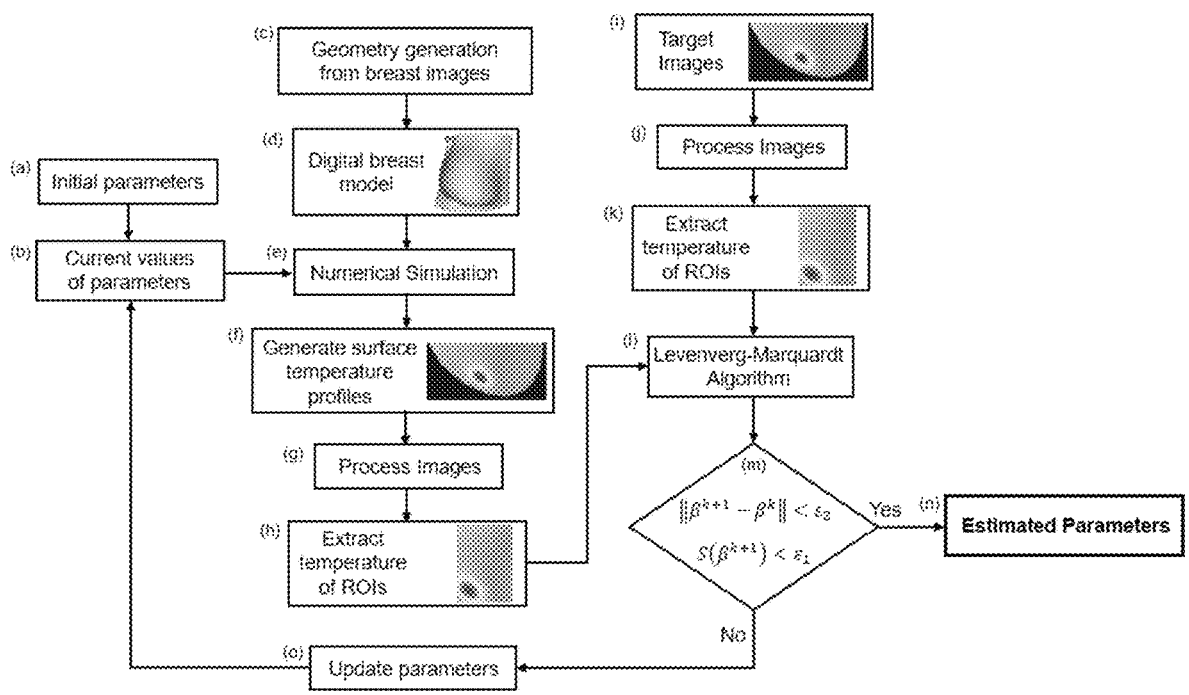
FIG. 23 is a flow chart of a method to estimate thermal parameters in a digital breast model in a prone position.

The metabolic activity of the tumor was obtained using the formula developed by Pennes, where dt is the tumor diameter:

$$q_t = \frac{3.27 \times 10^6}{468.5 \ln(100 d_t) + 50} \quad (2)$$

Where $q_t$ is the metabolic activity in W/m3 and $d_t$=0.027 m (2.7 cm) is the tumor diameter. Using (2) results in a value of the metabolic activity of 6,350 W/m$^3$. Using the parameters listed in Table 1, the thermal images were obtained. FIG. 20 shows the comparison of the clinical infrared images and the computed thermal images for three different positions. The digital model computed accurately the temperature distribution and predicted the thermal trends observed in the clinical infrared images.

The median temperature in each of the regions was computed, which allowed to filter the effect of small blood vessels. The absolute error between the clinical and computed temperature distributions was computed using:

$$E = \sum_{1}^{n_r \times n_c} |T_{exp,i} - T_{num,i}| \quad (3)$$

Where Texp and Tnum are the clinical and numerical temperature vectors, respectively, which contain all the individual temperature values of each of the individual regions. Table 2 lists the values of E, as well as the value of mean absolute error for each region. The mean absolute error per individual region is 0.12, which indicated that the model is accurately captures the temperature distribution observed in clinical images; therefore, the modeling approach is validated and can be used confidently to compute the temperature distribution for additional cases.

TABLE 2

Absolute error between clinical and computed thermal images.

| E [° C.] | E/$n_r$ × $n_c$ [° C./region] |
| --- | --- |
| 17.14 | 0.12 |

Example 7, Method C

The method described was used to estimate simultaneously five parameters named thermal conductivity of healthy tissue $k_h$, tumor size (diameter) d, tumor position within the breast ($x_t$, $y_t$, $z_t$) in a breast with cancer.

The parameters were estimated using a digital breast model (d) generated from a sequence of MRI images (c). A set of initial parameters (a) was used us current value of the parameters (b) to numerically solve (e) the governing equations to generate surface temperature profiles (f). The generated profiles were processed in Matlab (g, j). The temperature of various regions was extracted in both the numerical and target images (h, k). Both temperatures were compared using the Levenberg-Marquardt algorithm (l), if the convergence criteria (m) is not met, the parameters are updated (o) and the process is repeated. If the convergence criteria is met, the current value of the parameters is accepted as the estimated value of the parameters of interest. This process is outlined in FIG. 25.

A digital model of the female breast in prone position was generated from sequential Magnetic Resonance Imaging (MRI) images. The MRI images were individually filtered to reduce noise. Then, the outline of the breast was identified and the breast segmented in every slice. The sequential segmented images were stacked, which resulted in a digital breast model. This model was smoothed to generate a seamless and continuous breast model. The digital breast model was generated from the right breast of a 68-years-old woman with a grade III tumor and a diagnosis of invasive ductal carcinoma. The tumor was located at 12 o'clock, 2 cm from the nipple. The tumor volume was measured; although its shape is irregular, its volume was used to model a spherical tumor with a diameter of 2.7 cm and equivalent volume. Using Eq. (2) results in a tumor metabolic activity of $Q_t$=6350 W/m$^3$.

The Pennes' bioheat equation (1) was used to account for thermal interactions within the breast and with the environment.

Figure 24:
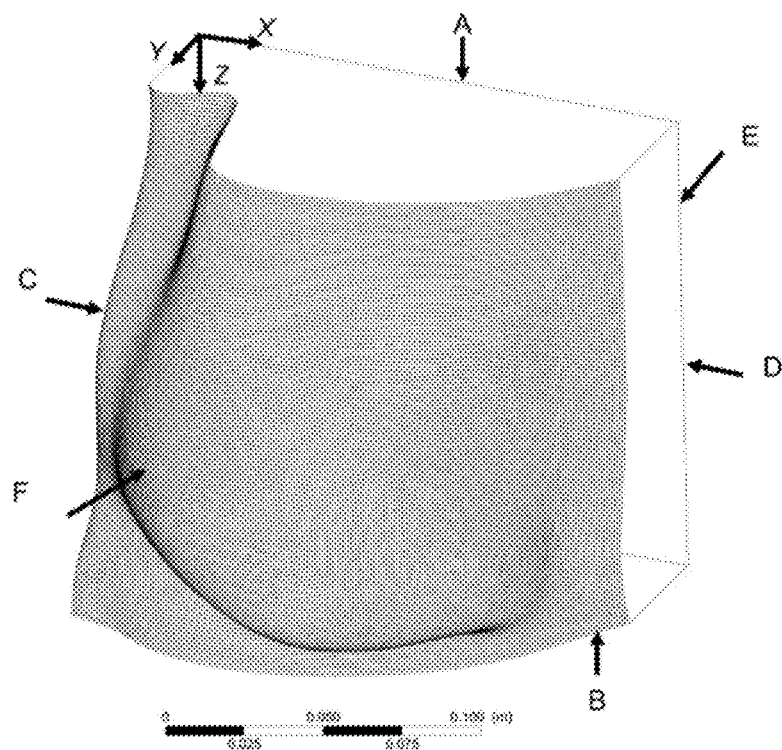
FIG. 24 shows a computational domain used in the simulations.

Pennes bioheat equation is subject to the following boundary conditions (FIG. 24): convection between the surface of the breast and the environment at Face F (4), constant temperature at the chest wall temperature $T_c$ at Face E (5), no heat flux across Faces 1, 2, 3 and 4 (6). In our computational model, we consider only two different tissues, gland (healthy) and tumor.

$$-k \frac{\partial T}{\partial n}\bigg|_{at F} = h(T_s - T_\infty) \quad (4)$$

$$T|_{at E} = T_c \quad (5)$$

$$\frac{\partial T}{\partial n}\bigg|_{at A,B,C,D} = 0 \quad (6)$$

The software ANSYS Fluent was used to numerically solve Pennes bioheat equation (1) in the digital breast model. This software uses the finite volume method to discretize the governing equation and provide a numerical solution for the problem. The perfusion and metabolic generation terms in (1) were introduced as source terms through User Defined Functions (UDFs). The UDFs allow to vary the tumor position and size without need to recalculate the mesh in the computational domain given a proper mesh; a mesh with 3.5 million elements was created for this purpose. The value of the constant parameters used to simulate the temperature distribution is shown in Table 3.

TABLE 3

Value of the constant parameters used in the simulations.

| Property | Value | Unit |
|---|---|---|
| Perfusion rate of healthy tissue ($\omega_h$) | $1.8 \times 10^{-4}$ | $s^{-1}$ |
| Perfusion rate of tumor ($\omega_t$) | $9 \times 10^{-3}$ | $s^{-1}$ |
| Metabolic activity of healthy tissue ($Q_h$) | 450 | $W\,m^{-3}$ |
| Temperature of arteries ($T_a$) | 37 | °C. |
| Specific heat of blood ($C_b$) | 3,840 | $J\,kg^{-1}\,K^{-1}$ |
| Density of blood ($\rho_b$) | 1,060 | $kg\,m^{-3}$ |
| Core temperature ($T_c$) | 37 | °C. |
| Ambient temperature ($T_\infty$) | 21 | °C. |
| Heat transfer coefficient (h) | 13.5 | $W\,m^{-2}\,K^{-1}$ |

A text file containing initial values of the five parameters was prepared to start the process of parameter estimation. The initial values were positive and in the range of values shown in Table 4. The range of values for the thermal conductivity was obtained from data reported in the literature; the minimum is for a completely fatty breast and the maximum is for an extremely dense breast. In the case of tumor diameter, the minimum value (9.9 mm) results in the maximum metabolic activity reported by Gautherie, the maximum is a 7 cm tumor, which would be easily palpable. For the case of tumor location, its center must lie within the computational domain.

TABLE 4

Range of values for the parameters to estimate.

| Parameter | Minimum Value | Maximum Value | Units |
|---|---|---|---|
| $k_h$ | 0.15 | 0.8 | $W\,m^{-1}K^{-1}$ |
| d | 0.0099 | 0.07 | m |
| $x_t$ | 0.06 | 0.16 | m |
| $y_t$ | 0.08 | 0.16 | m |
| $z_t$ | 0.08 | 0.15 | m |

Figure 25:
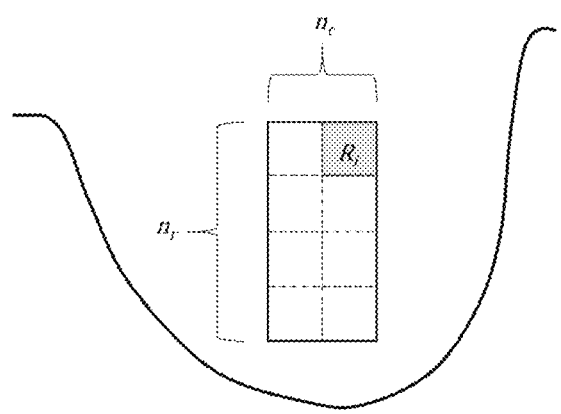
FIG. 25 shows a region of interest within the breast.

The surface temperature for each set of parameters was obtained through numerical simulations using the generated digital breast model. The technique was tested by estimating the parameter values from the target images using the technique described. In order to obtain the temperature along the entire breast surface, eight different views around the breast model were generated, each separated 45° clockwise in the XZ plane and oriented at 25° with the Y axis. The surface temperature distribution on the eight different views was exported as an image from ANSYS Fluent. The resulting images were read in MATLAB®. First, the region of the breast was isolated and the image intensity values were transformed to temperature values using an in house code in each of the eight images. Only the central part of each breast image was analyzed to avoid analyzing the same region in more than one image. Then, a rectangular region of interest (ROI) was defined in each of the images as shown in FIG. 25. The ROI in each image was divided into 12 rows by 6 columns. Resulting in $n_r \times n_c$ sub regions, $R_i$, in each of the eight images. The mean temperature of the pixels in each of the sub regions was computed and used to represent the temperature of each sub region. An arbitrary location was selected as the origin and all breast and tumor coordinates were adjusted accordingly. The initial tumor location was placed inside the central region of the breast.

We used the Levenberg-Marquardt algorithm to estimate the set of parameters β defined as:

$$\beta = [k_h\, d\, x_t y_t z_t]^T \tag{7}$$

the algorithm is used to minimize the objective function defined by:

$$S(\beta) = [T_{exp} - T(\beta)]^T [T_{exp} - T(\beta)] \tag{8}$$

The objective function (11) is the mean squared error between the experimental (target) temperature $T_{exp}$, and the current estimated temperature distribution T(β). The algorithm uses a damping parameter, μ, which value changes at every iteration and had an initial value of 0.001. A central difference scheme was used to compute each element of the Jacobian matrix, matrix formed by the derivatives with respect to the parameters, $$\frac{\partial T_i(\beta)}{\partial \beta_j} \approx \frac{T_i(\beta_j + \varepsilon \beta_j) - T_i(\beta_j - \varepsilon \beta_j)}{2\varepsilon \beta_j} \tag{9}$$

Once the Jacobian matrix is computed, the parameters are updated according with the equation:

$$\beta^{k+1} = \beta^k + [(J^k)^T J^k + \mu^k \Omega^k]^{-1} (J^k)^T [T_{exp} - T(\beta^k)] \tag{10}$$

Where the subscript k refers to the current value of parameters, and the subscript k+1 refers to the updated value of parameters. The matrix Ω is diagonal and its aim is to damp oscillations and instabilities by making its components large as compared to those of $(J^k)^T J^k$ if needed. The matrix Ω is defined as:

$$\Omega = \text{diag}(J^T J) \tag{11}$$

The algorithm used stopped stops when at least one of three conditions were met. In the first condition (12), the algorithm runs for a maximum of $k_{max}$ iterations, where $k_{max} = 50$ is used. In the second condition (13), the algorithm stops and accepts the current parameters as the best estimations when the objective function is lower than a small value $\varepsilon_1$, where $\varepsilon_1 = 10^{-3}$. The last condition (14), implies that the algorithm stops when the norm of the difference between current and updated parameters is lower than a value $\varepsilon_2$, where $\varepsilon_2 = 10^{-10}$. In this case, the updated parameters are accepted as the best estimations of the actual values.

$$k > k_{max} \tag{12}$$

$$S(\beta^{k+1}) < \varepsilon_1 \tag{13}$$

$$\|\beta^{k+1} - \beta^k\| < \varepsilon_2 \tag{14}$$

Using volumetric images of the breast with tumor helps to visualize the location of the tumor within the breast. FIG. 27 shows the actual tumor within the breast, the estimated tumor and the image registration between actual and estimated, where it is observed that the estimations match closely the actual location and size. The volumetric images with the estimated tumor can be useful in a clinical to aid in the location of the tumor for biopsy.

Example 8, Method D

Figure 28:
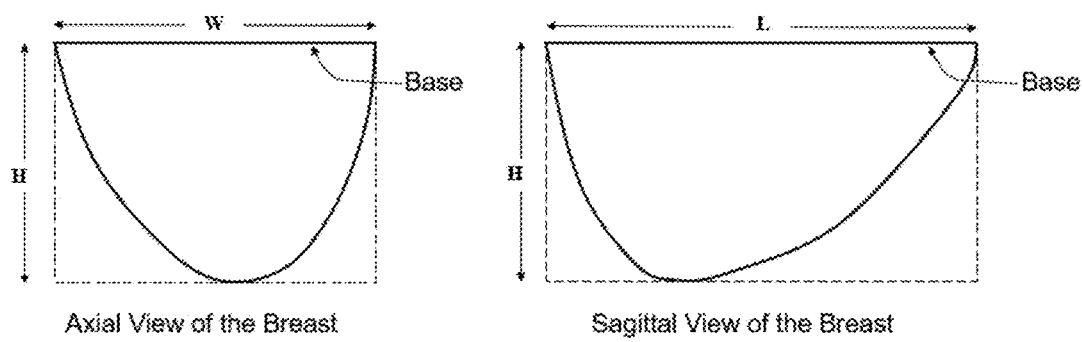
FIG. 28 shows Axial and Sagittal views of the breast to obtain geometric parameters.
Figure 29:
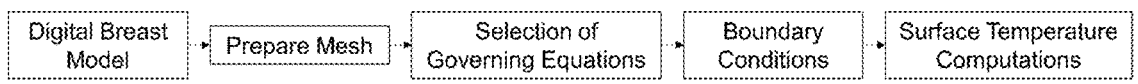
FIG. 29 is a flow chart of a procedure to compute phantom thermal temperature distributions from a 3D digital breast model.

The geometrical parameters that can be used include but are not limited to width (W), height (H), length (L), as seen from the images and any combination or function of these. A minimum of two images obtained from different views are necessary to categorize the breast. It is preferred to use images looking at the breast from the head (axial) and images looking at the breast from the side (sagittal) but any combination and number of images in any orientation can be used. The geometric parameters are measured from the base of the breast, which is a plane parallel to a Coronal plane. The base of the breast is identified as a plane parallel to the imaging table from the surface of the chest contacting the imaging table that can be located at any distance from the imaging table, one example could be that the base plane is coplanar to the bottom face of the imaging table. A rectangle surrounding the breast can be defined in any of the views to help in defining further indicators of the breast shape. The area defined by each of the rectangles is the maximum area that a breast with base and H dimensions can occupy in a scene. By computing the ratio between the actual area of the breast to the area of the rectangle, a fullness indicator is obtained. The fullness indicator, together with the other geometric identifiers are used to geometrically classify the breasts. An example of how to obtain the geometric identifiers from breast images is using FIG. 28.

From an axial view of the breast the following parameters can be defined using equations (15) and (16). From a sagittal view of the breast the following parameters can be defined using equations (17) and (18). Combining the information from the two views will define equation (19).

$$AAR = \frac{W}{H} \quad (15)$$

$$AF = \frac{\text{Breast area in view}}{WH} \quad (16)$$

$$SAR = \frac{L}{H} \quad (17)$$

$$AF = \frac{\text{Breast area in view}}{LH} \quad (18)$$

$$CAR = \frac{W}{L} \quad (19)$$

Any combination, function or power of these parameters can be used instead of the previously described. Other parameters that can be used to describe the breast shape and size is by mapping, fitting or matching the breast outline in any of the views to any algebraic, trigonometric, exponential or logarithmic function and provide the relevant parameters found.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for identifying suspected malignancy within tissue using thermal imaging comprising:
   a. constructing a geometric map of the surface of a body part;
   b. generating thermal indicators from a thermal infrared image of the body part surface;
   c. identifying a region of interest from the thermal indicators; and
   d. identifying suspected malignancy within the body part, wherein the thermal indicators within the region of interest identifying malignancy comprises thermal abnormalities indicative of the presence of a tumor if the temperature difference between maximum and minimum temperatures is greater than 0.5° C. over a 5 mm to 40 mm range and thermal abnormalities are classified as veins if the temperature difference between maximum and minimum temperatures is between 0.2° C. and 2.0° C. over a 1 mm to 5 mm range.

2. The method of claim 1, wherein the range indicative of the presence of a tumor is from 10 mm to 30 mm.

3. The method of claim 1, wherein an aspect ratio of length of the largest dimension to width of the smallest dimension of the region of interest between 1 and 4 is indicative of malignancy and an aspect ratio greater than 5 is indicative of a blood vessel.

4. A method for determining the presence of heat generating tissue in a body part, comprising:
   obtaining multi-view images of a body part, wherein the multi-view images comprise infrared images depicting a temperature distribution at the surface of the body part;
   obtaining a 3-D digital model representing the surface and internal tissue of the body part;
   generating a 3-D phantom thermal model by assigning values to selected parameters in the 3-D digital model of the body part and the surroundings and solving heat transfer equations, wherein the 3-D phantom thermal model comprises phantom thermal images of the surface of the body part;
   comparing the phantom thermal images of the surface of the body part with the infrared images depicting a temperature distribution at the surface of the body part; and
   identifying the values of the selected parameters generating the phantom thermal images matching the infrared thermal images.

5. The method of claim 4, wherein the parameters include thermal conductivity of healthy tissue, thermal conductivity of heat generating tissue, metabolic activity of healthy tissue, metabolic activity of heat generating tissue, perfusion rate of healthy tissue, perfusion rate of heat generating tissue, perfusion rate in an area affected by heat generating tissue due to increased vasculature from angiogenesis, temperature of tissue at selected locations, heat transfer coefficient, heat transfer boundary conditions, emissivity of skin surface, heat transfer parameters representing a surface of the body part and surroundings, size and shape of a heat generating tissue mass, 3-D location of a heat generating tissue mass, or combinations thereof.

6. The method of claim 4, wherein the selected parameters indicate a suspected malignancy.

7. The method of claim 4, wherein the 3-D digital model is obtained from the multi-view images.

8. The method of claim 4, wherein the 3-D digital model is obtained from a library of 3-D digital models representative of the body part.

9. The method of claim 4, wherein the matching is performed by an iterative process.

10. The method of claim 4, wherein the 3-D phantom thermal model is obtained from a library of 3-D phantom thermal models.

11. The method of claim 4, wherein the body part is a female breast.

12. The method of claim 4, wherein the multi-view images of the body part are obtained from an individual disposed in a prone position.

13. The method of claim 12, wherein the body part is a female breast, further comprising hanging both breasts freely from a table and pulling one breast out of the way with a separating fabric to obtain a clear view of the other breast being imaged.

14. The method of claim 4, wherein the 3-D digital model of the body part is generated from infrared, optical, ultrasound, magnetic resonance, outline capture techniques, shadow techniques, or X-ray multi-view images.

15. The method of claim 4, wherein the matching is conducted by iteratively improving the match between the surface infrared images and the phantom thermal images until a defined convergence criterion is met.

16. The method of claim 4, wherein the surface infrared images and the phantom thermal images are aligned using image registration in order to compare the surface infrared images and the generated phantom thermal images.

17. The method of claim 11, wherein various geometric identifiers comprising breast shape, breast size, breast circumference, distance from chest wall to nipple, or volume are utilized in obtaining the 3-D digital model from the library.

* * * * *